(12) United States Patent
Schechter

(10) Patent No.: US 7,065,400 B2
(45) Date of Patent: Jun. 20, 2006

(54) METHOD AND APPARATUS FOR AUTOMATICALLY PROGRAMMING CRT DEVICES

(75) Inventor: Stuart O. Schechter, Great Neck, NY (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 10/779,162

(22) Filed: Feb. 14, 2004

(65) Prior Publication Data

US 2005/0043895 A1 Feb. 24, 2005

Related U.S. Application Data

(60) Provisional application No. 60/496,595, filed on Aug. 20, 2003, provisional application No. 60/501,193, filed on Sep. 8, 2003, provisional application No. 60/501,648, filed on Sep. 10, 2003, provisional application No. 60/503,857, filed on Sep. 19, 2003, provisional application No. 60/506,604, filed on Sep. 27, 2003, provisional application No. 60/510,718, filed on Oct. 11, 2003, provisional application No. 60/515,301, filed on Oct. 29, 2003, provisional application No. 60/530,489, filed on Dec. 18, 2003.

(51) Int. Cl.
*A61N 1/36* (2006.01)
(52) U.S. Cl. ............................................... 607/2; 607/18
(58) Field of Classification Search ................ 607/4–5, 607/30, 32, 17–26
See application file for complete search history.

(56) References Cited

U.S. PATENT DOCUMENTS 5,156,154 A * 10/1992 Valenta et al. ............. 600/455

| | | | |
|---|---|---|---|
| 5,183,040 A * | 2/1993 | Nappholz et al. | 607/4 |
| 5,213,098 A * | 5/1993 | Bennett et al. | 607/18 |
| 6,070,100 A | 5/2000 | Bakels et al. | 607/9 |
| 6,539,261 B1 | 3/2003 | Dal Molin | 607/20 |
| 6,628,988 B1 | 9/2003 | Kramer et al. | 607/9 |
| 6,704,600 B1 * | 3/2004 | Daum | 607/30 |
| 6,708,061 B1 | 3/2004 | Salo et al. | 607/9 |
| 6,725,091 B1 | 4/2004 | Dal Molin | 607/2 |
| 6,760,623 B1 | 7/2004 | Stahmann et al. | 607/9 |
| 6,832,113 B1 * | 12/2004 | Belalcazar | 607/23 |
| 6,922,587 B1 * | 7/2005 | Weinberg | 607/9 |
| 2002/0002389 A1 | 1/2002 | Bradley et al. | 607/8 |
| 2003/0013977 A1 | 1/2003 | Daum | 600/508 |
| 2003/0097158 A1 | 5/2003 | Belalcazar | 607/32 |
| 2003/0204212 A1 | 10/2003 | Burnes et al. | 607/17 |
| 2004/0010293 A1 | 1/2004 | Holmstrom et al. | 607/9 |
| 2004/0015081 A1 | 1/2004 | Kramer et al. | 600/439 |

(Continued)

FOREIGN PATENT DOCUMENTS

EP 0 338 363 A2 * 4/1989

*Primary Examiner*—Carl Layno

(57) ABSTRACT

External or internal monitoring equipment is used to automatically determine optimal programming parameters for a CRT based on externally or internally derived measurements of cardiac performance, anisotropic myocardial deformation (AMD) or both. The ideal programming parameter, operational parameter, represents optimal interval timing between multiple electrodes within the CRT, and is generated by such a closed loop control system. The closed loop system may be semi-automatic and implement connectivity to external ultrasound equipment or externally derived measurements of transthoracic impedance. Preferably, the operational parameter is determined by a closed loop system using internally derived intracardiac and intrathoracic electrograms and impedance measurements that describe cardiac performance and electromechanical dysynchrony in real time. Such a CRT has a control system that automatically optimizes performance by a system of checks and balance.

16 Claims, 17 Drawing Sheets

U.S. PATENT DOCUMENTS

| | | | |
|---|---|---|---|
| 2004/0030356 A1 | 2/2004 | Osypka | 607/17 |
| 2004/0049235 A1 | 3/2004 | Deno et al. | 607/9 |
| 2004/0172080 A1* | 9/2004 | Stadler et al. | 607/17 |
| 2004/0186524 A1* | 9/2004 | Chinchoy | 607/17 |
| 2004/0215252 A1 | 10/2004 | Verbeck et al. | 607/9 |
| 2004/0220636 A1* | 11/2004 | Burnes | 607/17 |
| 2004/0220637 A1 | 11/2004 | Zdeblick et al. | 607/17 |
| 2004/0230229 A1* | 11/2004 | Lovett et al. | 607/4 |
| 2004/0230239 A1 | 11/2004 | Stahmann et al. | 607/14 |
| 2004/0243192 A1 | 12/2004 | Hepp et al. | 607/17 |
| 2005/0027320 A1 | 2/2005 | Nehls et al. | 7/9 |
| 2005/0038481 A1 | 2/2005 | Chinchoy et al. | 7/17 |

* cited by examiner

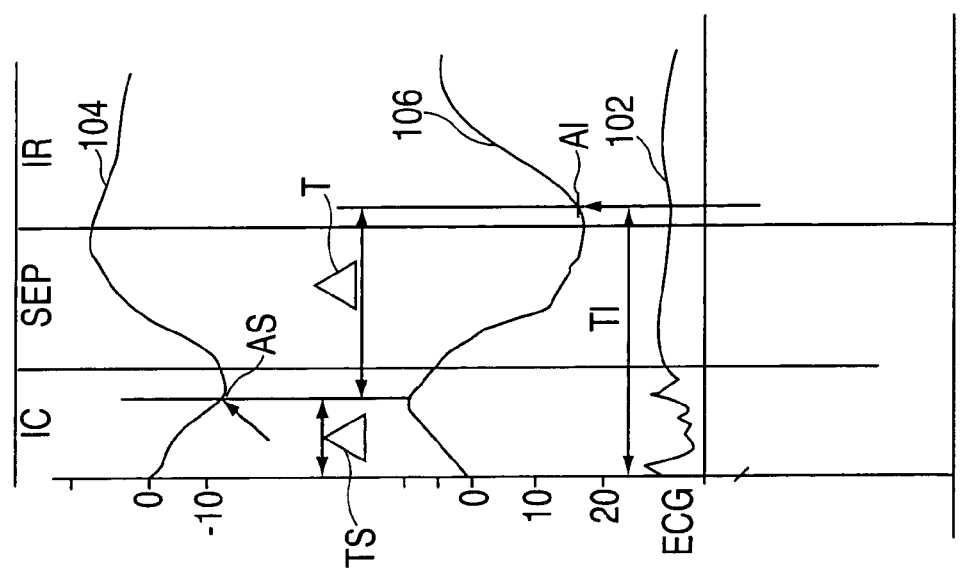
FIG. 4A
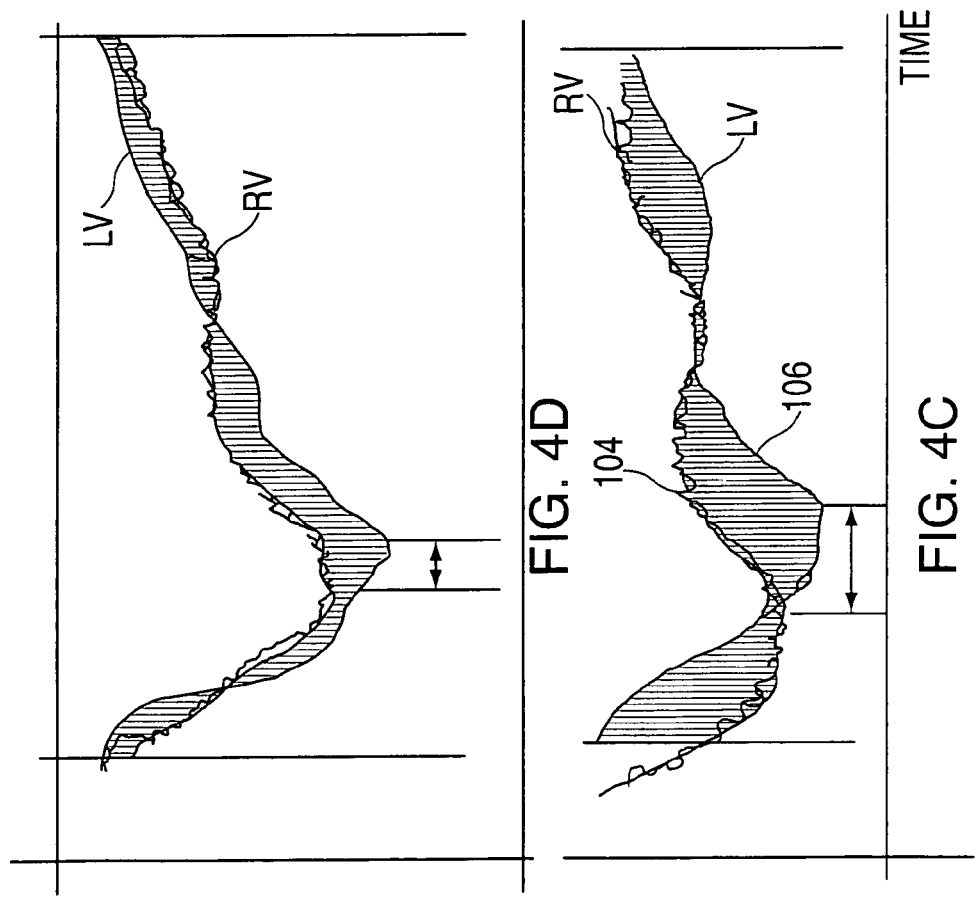
FIG. 4D
FIG. 4C

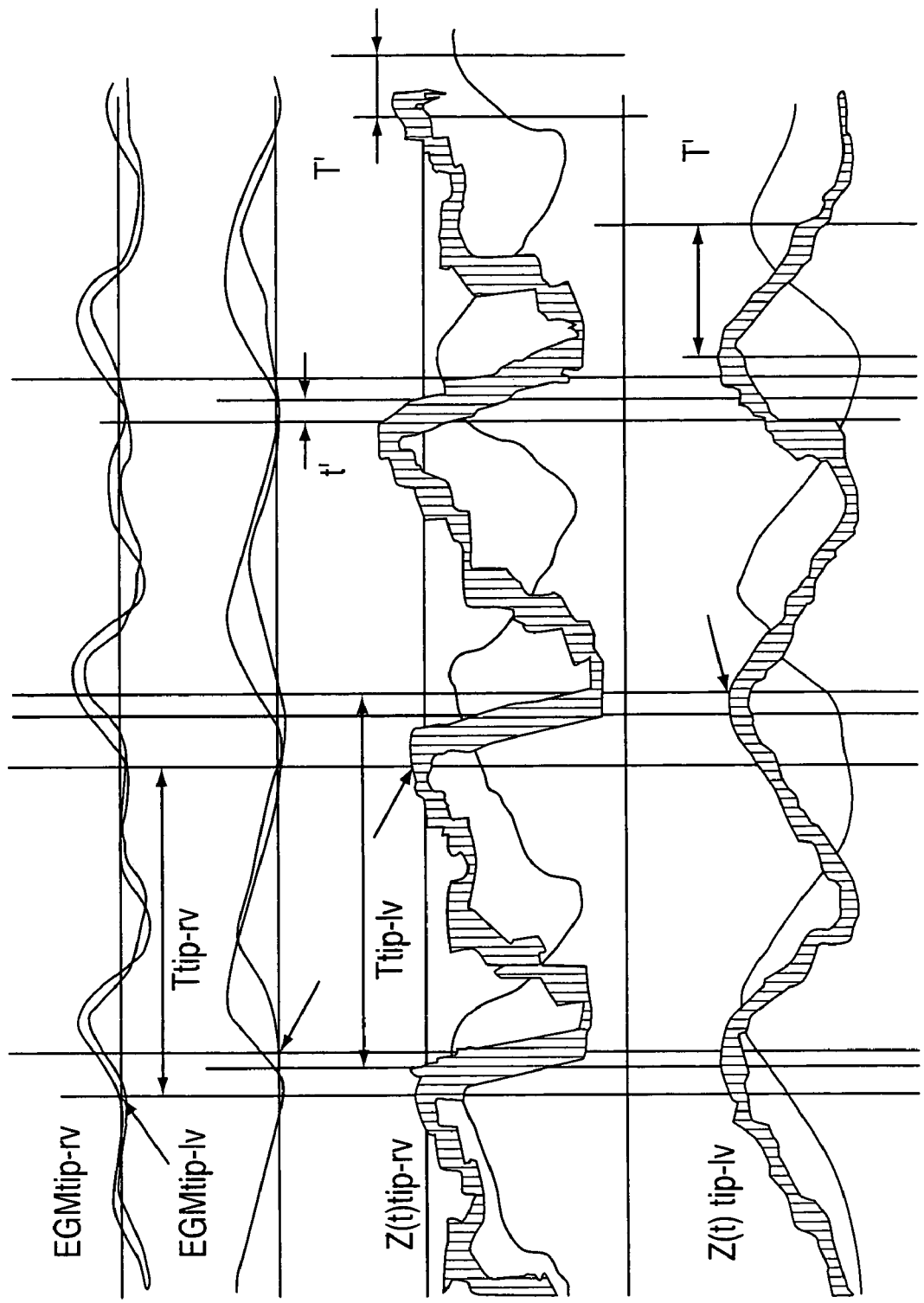

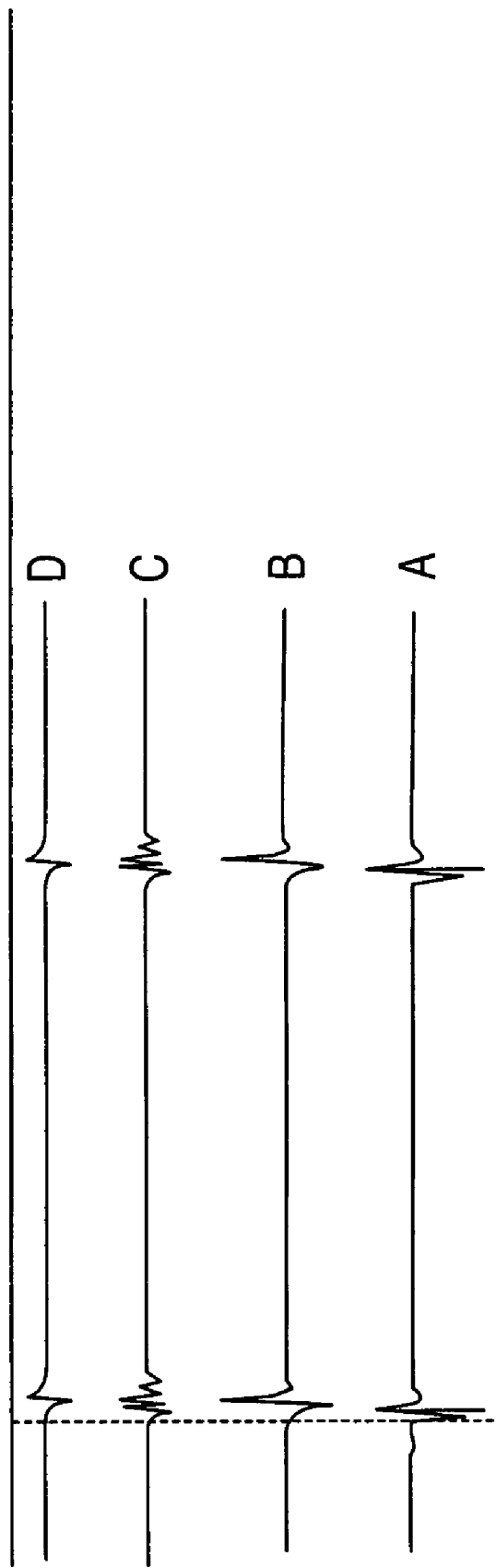

NORMAL Z(t) dt(top) and Z(t) dt with CHF (bottom)

IMPEDANCE CURVES, Z(t) OBTAINED ALONG CS LEAD ELECTRODES REFERENCED TO RV APICAL BIPOLE, r

METHOD AND APPARATUS FOR AUTOMATICALLY PROGRAMMING CRT DEVICES

RELATED APPLICATIONS

This application claims priority to provisional applications incorporated herein by reference:

Vital Monitoring System—Application No. 60/496,595; Express Mail No. ET 309088759 US; Filing Date Aug. 20, 2003;

Vital Therapeutic System—Electro-mechanical synchronization individually formulated by the Vital Monitoring System; patent pending; Application No. 60/501,193; Express Mail No. ET 39746886 US; Filing Date Sep. 8, 2003;

Vital Therapeutic System—(incremental myocardial recruitment) Patent Pending; Application No. 60/501,648; Express Mail No. ER 298051778 US; Filing Date Sep. 10, 2003;

Closed Loop Programming Of Temporal Correction Factors And Echo-Device Connectivity For Optimization Of Electro-Mechanical Synchrony. Application No. 60/503,857. Filing Date Sep. 19, 2003; Express Mail No. ER 298060029 US;

Correlates Of Electro-Mechanical Synchrony And Echocardiographic Assessments Of Strain—Filing Date Sep. 24, 2003; Express Mail No. ER 298053734 US—Confirmation of receipt by USPS tracking (signed by J. Steckel on Sep. 25, 2003) and by Return Receipt;

Closed Loop Programming of Temporal Correction Factors and Echo-Device Connectivity for Optimization of Electro-Mechanical Synchrony—Assessment of Integral Data, Slope, Time to Peak In Multiple Vectors; Application No. 60/506,604; Express Mail No. ER 298055885 US; Filing Date Sep. 27, 2003;

Rotational Symmetry and Synchrony—Patent Pending; Express Mail No. ER 837212141; Filing Date Oct. 10, 2004;

Vital Monitoring System—Variable Respiration Sensor—Patent Pending;

Vital Monitoring System—Advanced Diagnostic System-ADS; Application No. 512,824; Express Mail No. ER 597640626 US; Filing Date Oct. 20, 2003;

Global Cardiac Performance—Patent Pending; Application No. 60/515,301; Express Mail No. ER 640335729 US; Filing Date Oct. 29, 2003;

Closed Loop Programming of Temporal Correction Factors and Echo-Device Connectivity for Optimization of Electro-Mechanical Synchrony; Application No. 60/503,857; Filing Date Nov. 19, 2003;

Acute Monitoring System—Patent Pending; Express Mail No. ER 641505662 US; delivered Nov. 25, 2003;

Impedance as a Primary Variable and Purification of Global Cardiac Performance—Patent Pending; Express Mail No. ER 298144086 US; delivered Nov. 28, 2003;

Matrix Optimization Method—MOM—Patent Pending Express Mail No. ER 641493920; delivered Dec. 12, 2003;

Matrix Optimization Method—MOM II—Patent Pending; Express Mail No. ER 298144072; Filing Date Dec. 16, 2003;

Diagnosis of Dysynchrony Using Intracardiac Electrogram Data—Application No. 60/530,489; Express Mail No. 298152635 US; Filing Date Dec. 18, 2003;

VMS-ADS-IEGM—Patent Pending; Express Mail No. ER 298144055 US; delivered Dec. 29, 2003;

Ultrasonic Indices of Global Synchronization—Patent Pending; Express Mail No. ER 837212124; Filing Date Dec. 31, 2003

Patent Application I—Connectivity—Patent Pending; Express Mail No. ER 837188337 US; Filing Date Jan. 17, 2004;

Automatic Optimization Algorithm—Patent Pending ER 837185327 US; Filing Date Jan. 24, 2004;

Patent Application II—Connectivity—TCLS/AOA; Express Mail No. ER 352627522 US; Filing Date Jan. 28, 2004.

BACKGROUND OF THE INVENTION

1. Field of Invention

The present invention is related to implantable cardiac devices such as pacemakers and defibrillators that deliver cardiac resynchronization therapy (CRT), and to a method of programming devices using ultrasound or other techniques such as transthoracic or intracardiac impedance measurements to determine specific parameters indicative of the response of a patient to variations in cardiac stimulation patterns. The parameters are then used to direct closed loop programming of interval timing within such CRT device.

2. Description of the Prior Art

Impaired cardiac performance can result from several abnormalities. Such abnormalities include alterations in the normal electrical conduction patterns and mechanical abnormalities in myocardial contractility. These abnormalities are often (though not necessarily) connected to one another and, as such, electromechanical impairments can cause an impairment in cardiac performance as well. Such impairment in cardiac performance often stems from premature or delayed electrical and/or mechanical events in different cardiac chambers and within specific cardiac chambers. Newly developed cardiac resynchronization therapy devices have been developed as to correct this problem. Unfortunately, such devices do not improve a significant percentage of patients. This is a result of a general inability of such CRT to appropriately correct dysynchronous properties in a customized fashion for each particular patient. There currently are no control systems developed that can provide a tailored approach for resynchronization in individual patients.

Conduction abnormalities may occur between the atria and the ventricular chambers, atrial-ventricular dysynchrony. Abnormalities between right and left ventricular chambers (inter-ventricular) or within the right or left ventricles (intra-ventricular) can result in dysynchrony as well. Dysynchrony leads to ineffective work as a result of forces being generated in specific regions at inappropriate times relative to the opening and closing of the heart valves. It can lead to myocardial relaxation during times where the generation of force in all myocardial segments should be occurring synchronously and in a symmetric fashion in relation to valvular events and myocardial thickening when all myocardial segments should be relaxing, diastole, and receiving oxygenated blood from the lungs. Multiple variations in the location and pattern of dysynchrony may exist in individual patients.

The current understanding of electromechanical dysynchrony is in a state of evolution. Whereas it was once thought that the prolongation of electrical signals as demonstrated by a surface EKG was a specific indication of dysynchrony, more recent data supports that this is not necessarily accurate. Newer ultrasonic imaging modalities such as color Doppler myocardial imaging (CDMI) that quantify myocardial velocity and strain allow for qualification and quantification of myocardial dysynchrony. CDMI is more accurate for tracking synchrony and symmetry of cyclical cardiac events than any other imaging modality and offers the clinician the ability to appropriately program interval timing between stimuli applied by multiple electrodes in CRT devices best suited for an individual patient. However, CDMI does not provide any guidelines of how these timing intervals should be selected, and therefore the process of programming these intervals involves an effort based on trial and error and can be cumbersome and timely. Programming of appropriate interval timing will necessitate experienced physicians who are sub-specialized in the fields of electrophysiology and echocardiography. This will be difficult from a logistic standpoint especially at lower volume institutions or non-academic centers.

SUMMARY OF THE INVENTION

In one aspect of the invention, a method and apparatus is presented that provides a closed loop between CRT devices, a programmer and ultrasound equipment used to generate CDMI. The method and apparatus requires a shorter time to define optimal stimulation patterns (interval timing) and expedites programming of the CRT as multiple variables are able to be evaluated rapidly.

In another aspect of the invention, intracardiac impedance measurements are determined. An advantage of using measurements of intracardiac impedance is that this modality can be implemented for true closed loop programming of CRT devices rather than via connectivity to extrinsic ultrasound equipment. Using an ultrasonic interface at periodic intervals will help optimize such true closed loop programming and aid in determining interval timing with increases in heart rate, for example, during exercise. It also expedites the learning process that is ongoing in the fields of echocardiography and electrophysiology.

As strain measurements reflect myocardial thickening (systolic contraction) and thinning (diastolic relaxation), impedance measurements generated between transmyocardial electrodes will parallel such measurements of myocardial strain. The impedance value between transmyocardial electrodes increases with contraction and decreases with relaxation. Such a parallel will be useful for understanding the design of a system capable of true closed loop programming and for assisting the clinician in reprogramming such a system from time to time.

Two-dimensional or M mode imaging can describe the time and nature of valvular events, and corresponding intracardiac and trans-valvular impedance measurements will provide the same information. Through such an interface one can not only optimize interval timing between multiple electrodes in an expeditious fashion in the office setting but one can gain insights into how to best program CRT devices to accomplish this task using real-time trans-myocardial (regional), trans-valvular and trans-cardiac (global) measurements of impedance.

Importantly, true closed loop programming in such a fashion will become more readily implemented as modifications in lead technology and hardware configurations continue to evolve. In the interim an ultrasonic interface will help the clinician expeditiously optimize timing intervals in both academic and non-academic centers. Such an interface will also allow for dynamic changes in interval timing to be programmed as exercise echocardiography will determine the appropriate range for rate related changes in interval timing between multiple electrodes.

BRIEF DESCRIPTION OF THE DRAWINGS

In the following drawings, physiological curves are provided for illustrative purposes and are not based on actual patient data.

FIG. 4A shows typical strain curves for two regions of interest in the left ventricle;

FIGS. 4C and 4D show two strain curves superimposed during the cardiac cycle for a normal (synchronous) and an abnormal (dysynchronous) heart, respectively;

FIG. 10A shows intracardiac electrograms and impedance curves derived from multiple transcardiac electrodes which demonstrate electro-mechanical dysynchrony relative to normal template data;

FIG. 10C shows intracardiac electrograms obtained from the same lead in 10B after resynchronization;

DETAILED DESCRIPTION OF THE INVENTION

Figure 1:
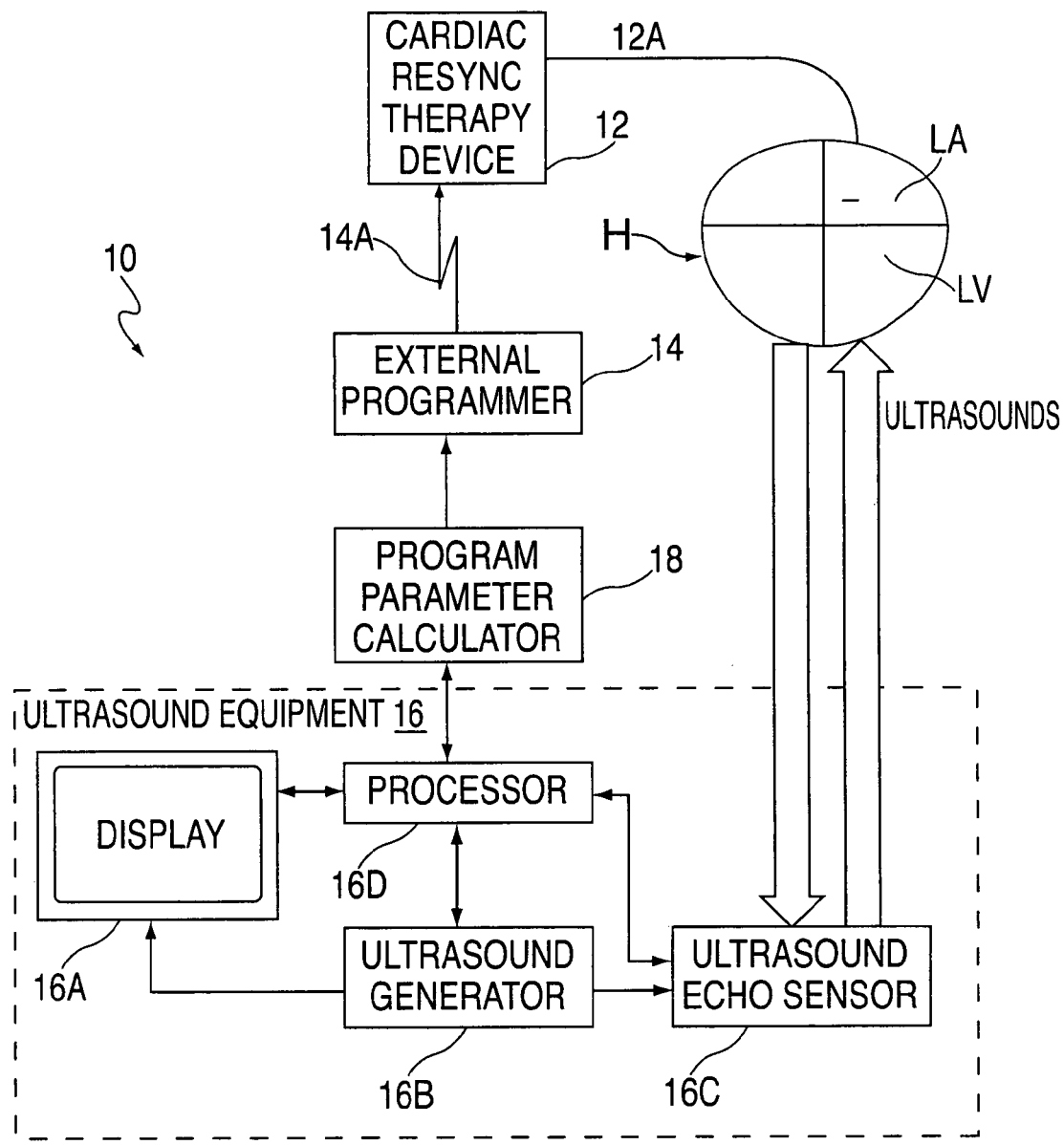
FIG. 1 shows a block diagram for an apparatus for programming a CRT device.

FIG. 1 shows an apparatus for programming a cardiac device such as a CRT (cardiac resynchronization therapy) device 12. The device 12 includes a lead or leads 12A with several electrodes positioned to provide sensing and excitation in a patient's heart H, as discussed in more detail below, including sensing and pacing of at least the right atrium and right and left ventricles [left atrial leads not available but under development via stimulation through the coronary sinus or alternate form]. For the sake of simplicity, the electrodes have been omitted.

The apparatus 10 further includes a programmer 14 with a wand 14A. The wand 14A is used to transmit data from the programmer to the device 12. As part of this process, the device 12 receives commands to send stimulation signals to the respective cardiac chambers, and to sense the corresponding cardiac response, as discussed in more detail below.

The apparatus 10 further includes ultrasonic equipment 16. The ultrasonic equipment 16 includes a display 16A, an ultrasound generator 16B and an ultrasound echo sensor 16C. These elements are controlled by a processor 16D. Ultrasonic display 16A displays images derived from reflected ultrasound waves generated by the ultrasound generator, 16B, and received by ultrasound sensor, 16 C, after processing in processor, 16D. The processor, 16D, receives the echoes and provides various information for a user such as a cardiologist or a clinician through the display 16A. The display 16A may include either a touch screen or other means (not shown) through which the user can provide input to the processor 16D. For example, the user may select portions of an image on the display 16D and request further information associated with the selected portions, request further data processing associated with the selected portions, or request some other data manipulations as discussed below.

The display 16A may show, directly, or indirectly, a live picture of the heart and its tissues, the operation of the valves and some parameters such as blood flow, myocardial thickness, myocardial velocity/strain, ejection fraction, cardiac dimensions, and so on. Ultrasound equipment of this type is available, for example, from GE, ACUSON and Philips.

Importantly, according to this invention, there is also provided a program parameter calculator 18 that operates in an automatic or semi-automatic mode to determine the programming parameters for the device 12. The calculator 18 is shown in FIG. 1 as a separate element, but it can be incorporated into the programmer 14, the ultrasound equipment 16 or even the device 12.

Figure 2:
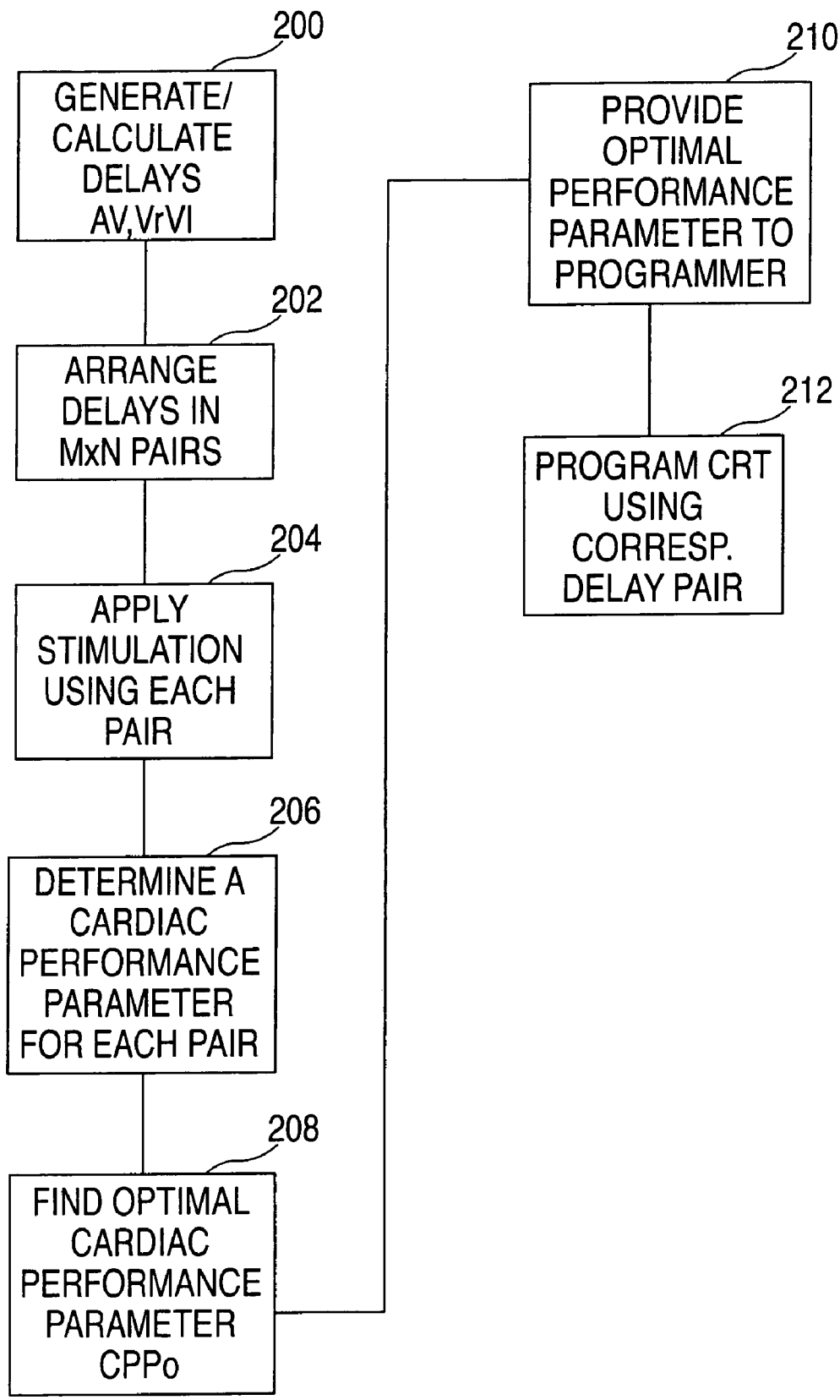
FIG. 2 shows a general flow chart for the operation of the apparatus of FIG. 1.

The general operation of the apparatus 10 is now explained in conjunction with the flow chart of FIG. 2. In step 200 one set of AV (atrial-ventricular interval) and VrVl, interval (programmed delay time between stimulation between electrodes in the right and left ventricles) and, optionally, other delays which may relate to intraventricular time delays, VaVb, (e.g. the delay time between stimuli delivered to a posteriorly positioned coronary sinus LV lead, Va, and laterally positioned coronary sinus LV lead, Vb) associated with the operation of the CRT 12 are selected. This can occur either automatically by the program calculator 18, or manually. Alternatively, these delays may be preprogrammed parameters. As described, the AV delays are between the right or left atrial and the right or left ventricular pulses, the VrVl delays are between the left and the right ventricular pulses and VaVb are between other electrodes (e.g. multi-site coronary sinus left ventricular electrodes). For example, five AV delays may be selected at 90±20 msec in 10 msec intervals (e.g., 70, 80, 90, 100, 110) and five VrVl delays may be selected at 0±20 msec in 10 msec intervals. Of course, any number M AV delays may be used and N VlVr delays may be used. The one set of delays form M×N delays times. These delays may be arranged into a two dimensional array or matrix for computational purposes (step 202). If three (or more) delay times (e.g. multiple interval timing, AV, VrVl, VaVb) are programmed then a multi-dimensional matrix can be used for computational purposes and M×N×P delay times will be analyzed. Importantly, the AV can be predetermined using commonly employed equations (e.g. Ritter method) and not act as a variable for this matrix. With the predetermined AV delay programmed, only variables VrVl and VaVb need be evaluated using a two rather than a three dimensional matrix. This will reduce the number of delay times evaluated by this methodology. If 2 atrial leads are employed, RA and LA, the AV can reflect the time interval between the last stimulated atrial chamber (e.g. LA) and first stimulated ventricular chamber (e.g. RV) and be preprogrammed. The matrix optimization method described above can then apply to interval timing between the RA and LA and VrVl. As is readily apparent a number of permutations are possible which depend on the lead/electrode configurations implanted within a particular patient.

Next, in step 204 the CRT device is operated by the programmer 12 to stimulate the heart H sequentially using the set of delays defined in step 200. For example, the stimulation may be applied first using pulses with an AV delay of 70 msec and a VrVl delay of −20 msec.

In step 206, a predetermined cardiac performance parameter CPP is chosen. This parameter is indicative of the performance of the heart H responsive to these delays (e.g. Aortic Velocity Time Integral, AoVTI; TEI index). The user can be signaled to obtain this CPP using the ultrasonic equipment 16. Alternatively, the ultrasonic equipment may obtain CPP data automatically. Next, the heart is stimulated again using an AV of 80 msec and a VrVl delay of −20 msec, and another CPP is derived. Altogether, the heart is stimulated MxN times and a corresponding CPP is derived for each stimulation pattern (set of delays). The CPP can be obtained over a specific number of cardiac cycles and a mean value of CPP is derived over this specific number of cardiac cycles.

As described in more detail below, these performance parameters are preferably collected automatically by the ultrasonic sensor (and/or by other means) and provided to the program parameter calculator.

In step 208, the program parameter calculator identifies a cardiac performance parameter CPPO that provides the optimal cardiac performance (or, at least, the parameter that comes closest to optimal performance).

In step 210, the pair of delays AVx, VlVrx corresponding to the optimal cardiac performance parameter is provided to the programmer 12.

In step 212 the programmer 12 programs these delays into the CRT.

Many different cardiac characteristics could be used as the CPP. For example, the CPP may be the ejection fraction. However, at present this characteristic is rather difficult to measure accurately and is subject to operator dependency. Therefore the present inventor has identified several other parameters that can be used as the CPP. One of these characteristics is the aortic velocity time integral or AoVTI. The velocity of the blood through the aortic valve or aortic outflow tract is one of the parameters that is determined and displayed by the ultrasonic equipment 16 and shown in display 16A as a curve, as indicated on FIG. 3. During step 206, the processor 16D integrates under the velocity curve shown in FIG. 3 to obtain a parameter AoVTI. This step may be performed either after a clinician selects the curve on the display and requests its integral, or can be performed automatically, by the processor 16D without any prompting by the clinician. In this manner respective values of AoVTI are calculated for each set of delays. These values are then provided to the calculator 18 and processed as discussed above. As part of the process, the AoVTI having the largest value is determined, i.e., AoVTImax is determined as the optimal AoVTI. In other words, the AoVTImax is the optimal cardiac performance parameter.

However, the present inventor has discovered that other types of parameters may be more useful for the programming of the CRT. More specifically, quantitative parameters indicative of myocardial dysynchrony or anisotropic myocardial deformation (AMD) in a patient are also important for CRT programming. Though any quantitative analysis of anisotropic myocardial deformation may be utilized, the inventor has identified several such parameters discussed below.

Figure 4:
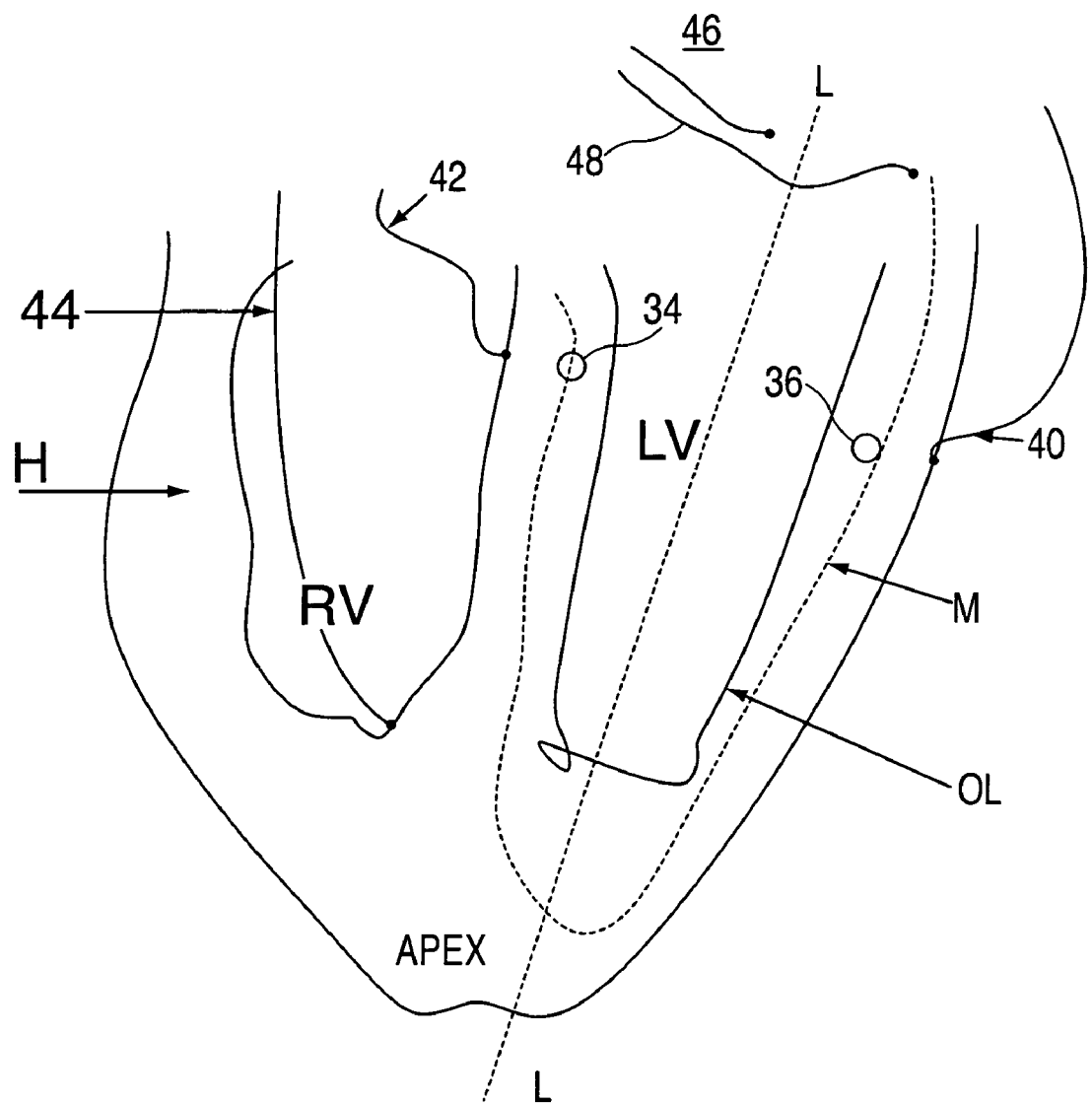
FIG. 4 shows details of a heart as seen on the monitor (apical 4 chamber (atria deleted for simplification purposes) of the apparatus of FIG. 1.

One parameter that is indicative of AMD is related to myocardial strain derived from myocardium using Color Doppler Myocardial Imaging, CDMI. Strain is measured using the ultrasonic equipment 16. FIG. 4 shows diagrammatically a portion of the heart H as seen on the display 16A. On this rendering two portions of myocardium, regions of interest, 34 and 36 are selected. These regions of interest can be selected manually by the user. Alternatively, the portions 34, 36 could be selected automatically by the ultrasonic equipment 16 or the calculator 18. Preferably these regions of interest, 34, 36 should be selected so that they are symmetrical with respect to a central longitudinal axis, L—L of the left ventricle. Determination of these regions of interest can be made automatically by ultrasonic equipment 16 determining the myocardial segments with the most significant dysynchrony (e.g. left ventricular basal lateral wall) and the symmetrically located region without dysynchrony (e.g. basal interventricular septum).

As shown in FIG. 4A, the ultrasonic equipment 16 then determines and displays myocardial strain curves on the display 16A associated with these portions during one or more cardiac cycles. In FIG. 4A a typical ECG is represented by curve 102, the strain on portion 34 on the septum is represented by curve 104 and the strain associated with lateral ventricular wall at the portion 36 is represented by curve 106. For a normal heart, the two curves 104, 106 are substantially identical and occur during the systolic ejection phase, SEP, of the cardiac cycle. However, for a patient with an abnormal heart, the two curves are offset in time and may differ in other aspects as well. For example, the minimum amplitude As (this point on curve is actually maximal strain as the direction of relative myocardial velocities/strain is opposite to the transducer location) for curve 104 occurs at a time Ts from initial depolarization while the minimum amplitude AI for curve 106 occurs at a time TI from initial depolarization. Initial depolarization is defined by the QRS complex on the simultaneously acquired ECG.

It is believed that the reason for this intra-ventricular dysynchrony or anisotropic myocardial deformation within the left ventricle, is secondary to regional electromechanical abnormalities. In order to correct this problem, the heart H should be paced in such a manner that the peak strain or amplitudes occur at a similar time. Importantly, the region which manifests electro-mechanical delay is stimulated earlier (delta T in figure) in the cardiac cycle so that it behaves synchronously with a corresponding symmetrically located portion of normally activated myocardium. For this purpose, a strain correction factor index, SCFI, is defined as the AMD parameter. For example, SCFI could be Ts/TI. An SCFI is calculated for each of the pair of delays discussed above. The optimal AMD parameter in this case is the SCFI closest to unity.

Figure 4B:
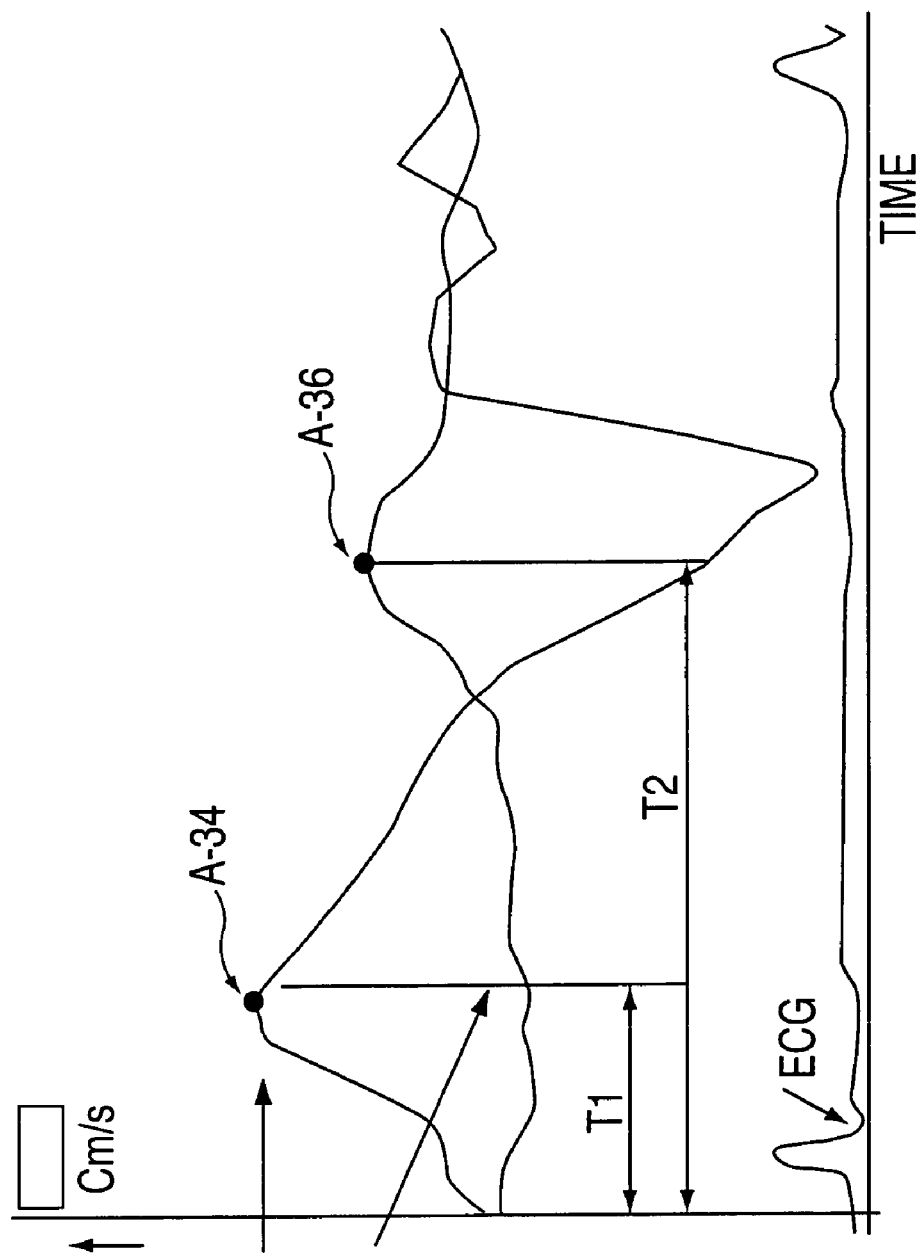
FIG. 4B shows typical velocity curves for two regions of interest in the left ventricle.
Figure 4E:
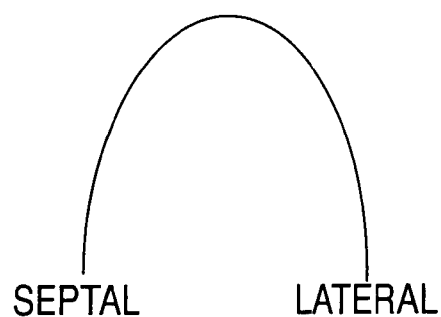
FIG. 4E shows curved M-mode data acquisition and the line defining the end-diastolic turnaround time, EDTT, the time of aortic valve opening, AoVo, and the area between, systolic myocardial relaxation integral, SMRI.
Figure 4F:
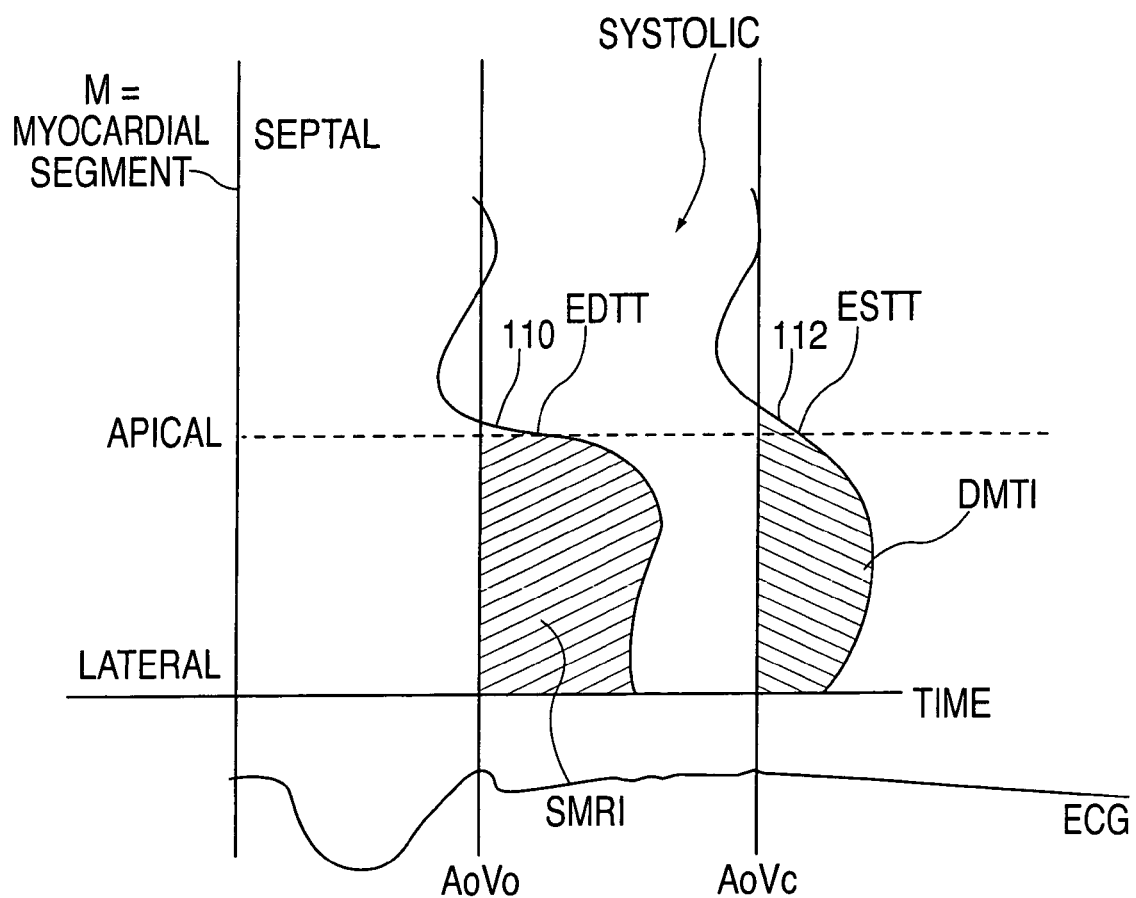
FIG. 4F shows curved M-mode data acquisition and the line defining the end-systolic turnaround time, ESTT, the time of aortic valve closure, AoVc, and the area between, diastolic myocardial thickening integral, DMTI.

Another characteristic that can be used as an AMD parameter associated with the ventricular chamber tissue portions 34, 36 portions is a parameter associated with their motion. During a typical cardiac cycle, the various portions of tissues forming the ventricular chamber travel at different rates, with the tissues at the apex typically traveling at the lowest velocity. Myocardial longitudinal velocity during systole is toward the apex of the heart and in the opposite direction during diastole. The velocities of the regions can be measured by the ultrasonic equipment 16. The resulting velocity profiles or typical for regions 34, 36 are shown in FIGS. 4B. In this example, the two points analyzed on these curves are maximum points A34 and A 36, occurring at T1 and T2 after the initial depolarization of the ventricle. One can use an alternate point such as the point defining the initiation of motion in these regions of interest as well. A velocity correction factor index, VCFI, is then defined as T1/T2. As with SCFI, this parameter is optimal when it approaches unity. Analysis of measurements of myocardial velocity will be more representative of synchrony related to changes in interval timing while analysis of measurements of myocardial strain will be representative of both relative motion and properties of contractility. Differences in these data sets can be used to differentiate properties of electrical and mechanical dysynchrony and can be used to describe areas of myocardial scarring from heart attacks and areas of myocardial viability where resynchronization therapy will more favorably remodel ("heal") regional myocardium that has been deprived of normal electrical stimulation patterns. This vital data can be utilized for monitoring purposes.

In another embodiment of the invention, other characteristics of the curves 104, 106 are used. FIGS. 4C and 4D show two such superimposed curves obtained from regions 34, 36, for example, representing strain. The curves in 4C are from a patient with dysynchrony prior to optimization of interval timing and the curves of FIG. 4D are the strain curves for a patient without significant AMD after optimal delay times have been programmed. According to this embodiment, a difference integral function (DIF) is derived by taking the integral of the difference between the two curves shown in FIGS. 4C and 4D as a function of time over a cardiac cycle (or cardiac cycles using summation or ensemble averaging). Similar ensemble averaging techniques can be used to analyze myocardial segments (multiple neighboring regions of interest) where multiple strain curves are derived over a sequential number of cardiac cycles. The optimal DIF is the index with the smallest value, minimal integral difference, MID. This MID is then used as the AMD parameter. Alternatively, instead of the difference, a correlation function that compares the two curves can be used to define an AMD parameter. Moreover instead, of the strain curve, the MID can be determined using the velocity curves of FIGS. 4A and 4B.

In order to generate the curves of FIGS. 4A–4D, the ultrasonic sensor is operated in a 2D mode, and either the user manually selects regions of interest or such regions of interest are automatically selected from a myocardial segment that has the most prolonged time to peak velocity (or strain) and a normal segment that is located in a symmetric region of interest about the central longitudinal axis, LL.

Figure 3:
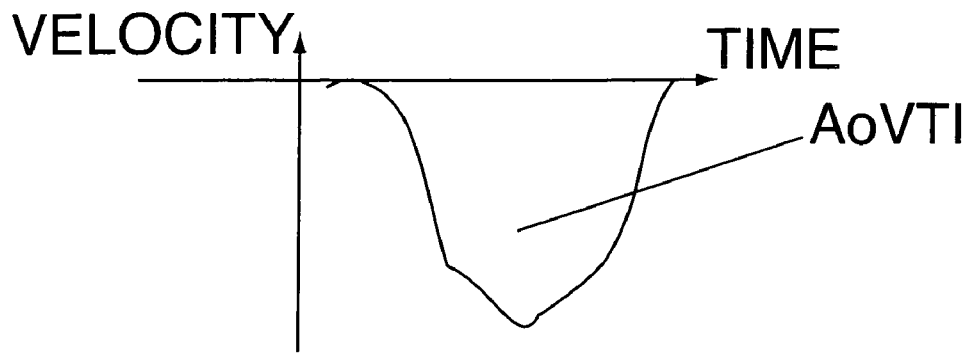
FIG. 3 shows a time-dependant graph of a typical Doppler derived aortic velocity time integral, AoVTI, during a cardiac cycle obtained from a sample of blood flow coursing through the aortic valve. This integral describes the flow of blood through the aortic valve over time and is a representation of cardiac performance.

Another mode of operation of the sensor is determined by signals generated by curved M-mode. In the curved M-mode, instead of two regions, a straight or a curved line M is selected that is traced around the left ventricle, through the myocardium as shown in FIG. 3. As for the previous embodiments, the curve M is selected either manually by the user on the display 16A or automatically. For example, the ultrasound equipment 16 first detects the outline OL of the inner left ventricle using automatic edge or border detection algorithms and then selects the line M so that it lies outwardly of the outline and spaced therefrom by a predetermined distance, such as 3–5 mm. Once this line is provided to the processor or automatically determined by the processor 16D, then various graphical analyses are performed on this line, including, for example myocardial velocity data for all myocardial tissue that is sampled along this line during a cardiac cycle. This velocity defines how these segments are moving longitudinally (toward the apex during systole and away from the apex during diastole). This information yields more comprehensive data than the discrete regions 34, 36 discussed above. For example, in Figure the curve 110 occurs at the end of myocardial relaxation for all segments and is defined as the end diastole turnaround time, EDTT, or the time when all segments change direction and begin to move from base to apex. This indicates the abnormal movement of myocardial segments in a pathological heart that are still relaxing and have not started contracting until a delayed time period after aortic valve opening has occurred, line AoVo. These segments can not generate force or cardiac output at the appropriate time (dysynchrony) in these pathologic segments as a result of delayed electromechanical activation. Integrating the area between this curve and the line that delineates aortic valve opening yields a new parameter, systolic myocardial relaxation integral (SMRI). Similarly, the diastolic myocardial thickening integral (DMTI) can be derived by determining the area between the end of myocardial thickening for all segments (end systolic turnaround time, ESTT, or the time when all segments change direction and begin to move from apex to base, curve 112) and the time of aortic valve closure, AoVc. Either of these integrals can be used as the AMD parameter. The parameters are optimized when they have the smallest value. The timing of aortic valve opening and closure can be extrapolated to the surface ECG from the appropriate imaging planes and used as a reference in patients with regular rhythm.

Relative delays in electromechanical activation in certain myocardial segments may occur within the time frame of the systolic ejection period (not before or after aortic valve opening or closure, respectively) but remain dysynchronous. Such relative delays can be evaluated by adjusting the pulse repetition frequency as to cause aliasing of the myocardial Doppler signal at any point within the systolic time frame. Evaluating the symmetry or lack of symmetry of onset of aliasing with such curved M mode aliasing velocity data can provide a window into more subtle anisotropic myocardial deformation and can be used as a quantitative parameter in a similar fashion as the DMTI and SMRI described above.

Figure 4G:
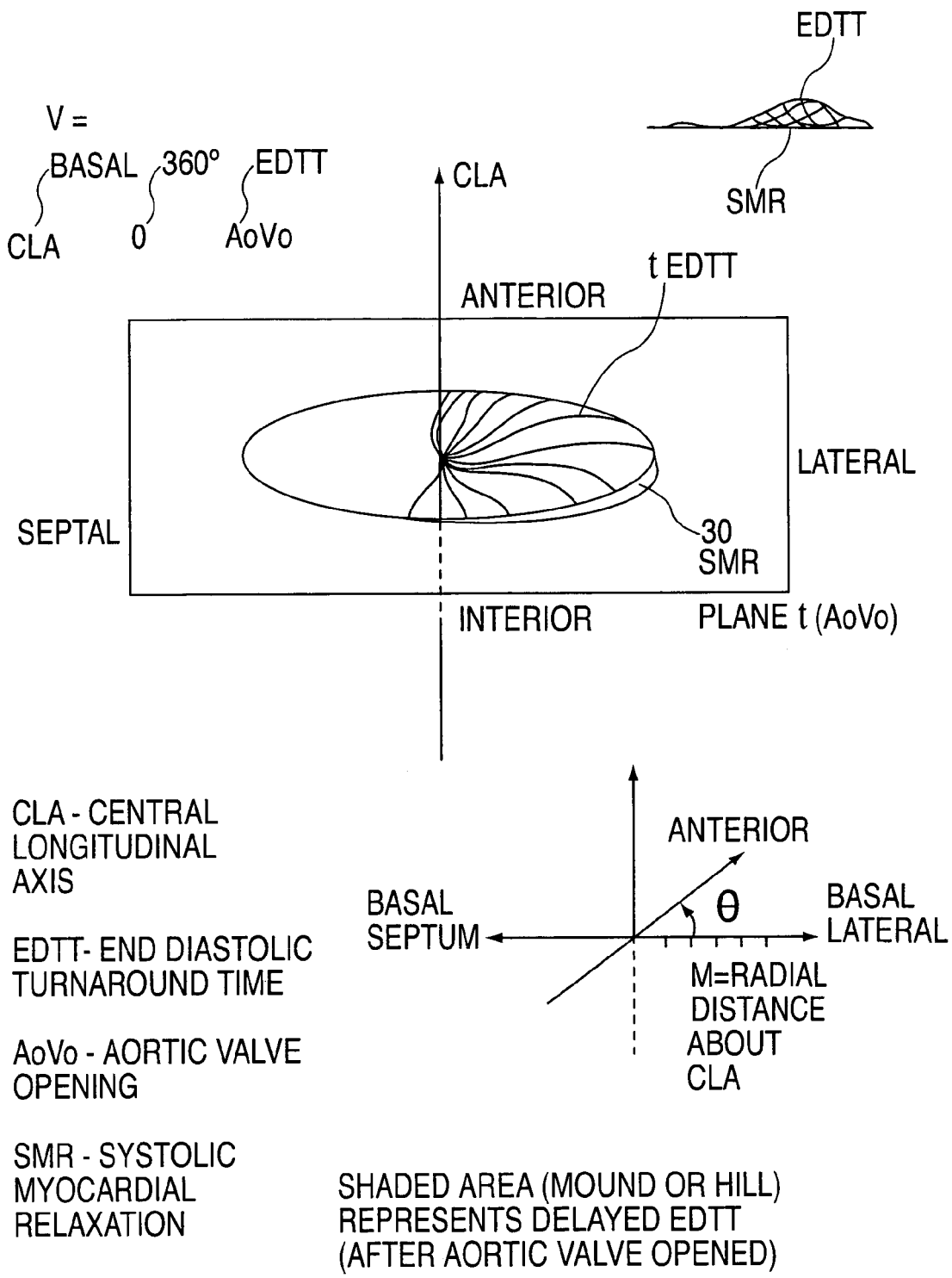
FIG. 4G shows multi-dimensional representation of curved M-mode data with interpolation as to create the end diastolic turnaround time surface, S, and volume, V, between surface S and plane, AoVc, which represents the volume of delayed dysynchronous myocardium in three dimensions as a triple integral calculated in polar coordinates.

Moreover, more complex manipulations may also be performed on curves 110 or 112 (as is demonstrated using curve 110 in FIGS. 4G). For example, integrating the curve in three dimensions results in a volumetric parameter, V, indicative of the actual volume of dysynchronous myocardium over time. This can be derived using newly developed ultrasound transducers that can provide three dimensional data by essentially rotating the line M through the heart tissues about axis L—L and obtaining a three dimensional shape indicative of the velocity of multiple myocardial segments about the left ventricle. This shape may be analyzed using polar coordinates to obtain a multi-dimensional AMD parameter. Myocardial radial distance, angle about L—L, and time represent the coordinates for such an analysis. The time between aortic valve opening and EDTT's determined for multi-dimensional curved M mode data acquisitions represent the integral limits for such quantitative representation of AMD. Interpolation between the acquired EDTT lines will be necessary to form the upper surface representing the upper limit of integration. The lower limit of integration is the plane describing aortic valve opening. In this example, the volumetric parameter, V, represents all dysynchronous myocardial tissue that is relaxing (should be contracting) after the aortic valve has opened.

In another embodiment of the invention, several different types of AMD parameters are calculated for each set of delays (such as SCFI, VCFI, MID, DTMI, SRMI, etc.). The AMD from each parameter is determined and then the AMDs from the different parameters are compared. The parameter representing the minimal AMD is then selected as the parameter to be used for programming of the CRT. AMD parameters not yet described can also serve as a means to quantify dysynchrony and be implemented for this invention.

Figure 6:
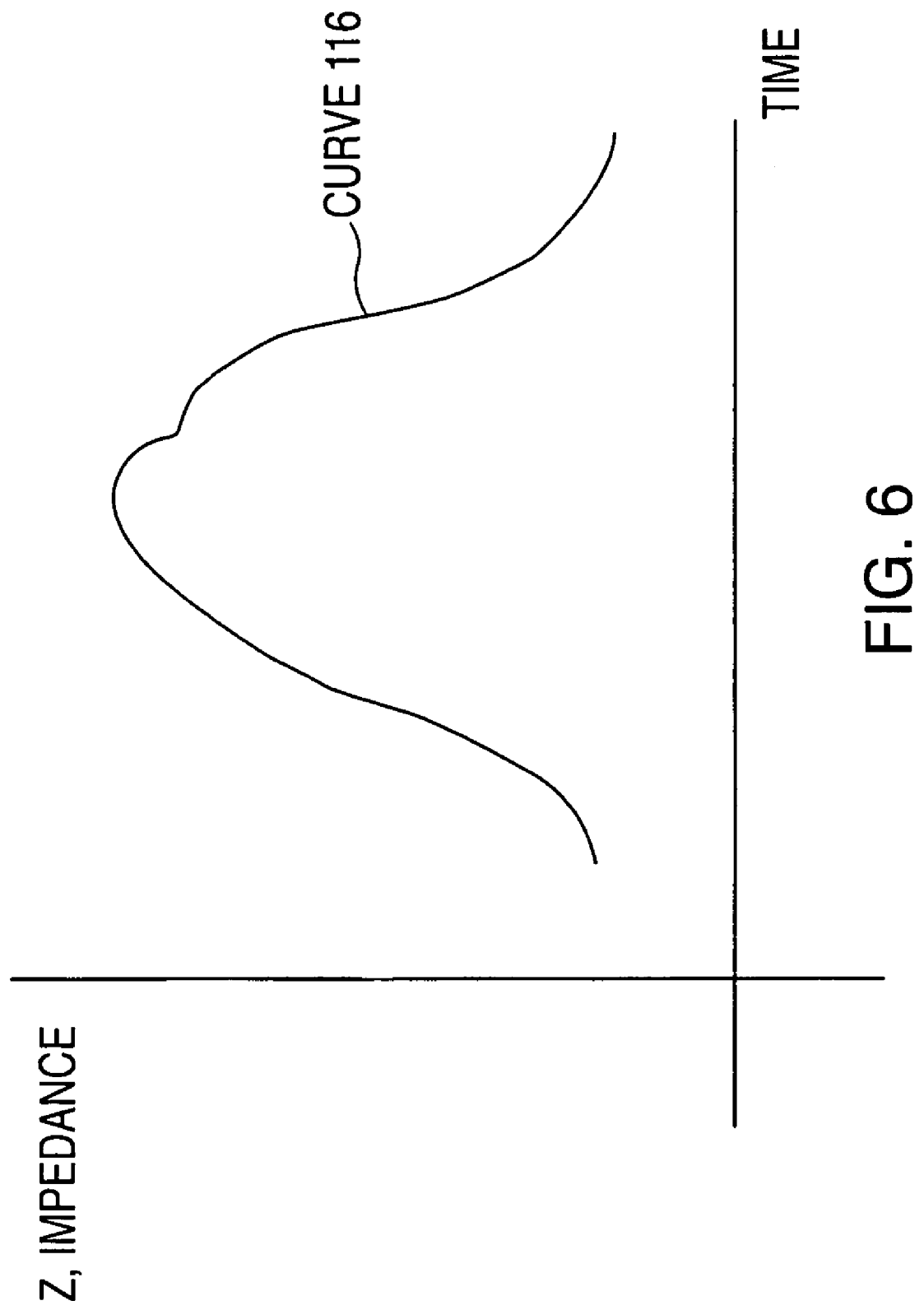
FIG. 6 shows a time dependent transthoracic impedance curve, 116, representing changes in blood volume within the aorta and great vessels which relate to measurements of cardiac performance.

In another embodiment of the invention, an apparatus 10A is disclosed in which the cardiac performance parameter is derived by means of transthoracic impedance cardiographic equipment 20 instead of the ultrasonic equipment 16. The impedance cardiographic equipment 20 is similar to ultrasonic equipment 16. It has a display 20A, a current generator 20B, electrodes 20C and a processor 20D. The electrodes 20C are first placed across the thoracic area of the patient and the current generator 20B applies a current between the electrodes. Sensors within the electrodes 20C are then used to determine the voltages induced by this current. Transthoracic impedance monitors of this type are available from Cardiodynamics of San Diego, Calif. Using this monitor, a time dependent impedance curve is derived, as shown in FIG. 6, with the curve 116 representing impedance changes related to changes in blood volume within the aorta and great vessels. One or more characteristics of this parameter are then used as a CPP. These characteristics may include cardiac output, cardiac index, stroke volume or any other data obtained or calculated from the transthoracic impedance equipment. The timing of data acquisition with impedance cardiographic equipment 20 can be optimally triggered by intracardiac electrograms obtained from electrodes derived from a specified lead, 12A. Such timing is best initiated by defining the onset of the cardiac cycle, systole, measured by ventricular electrograms obtained from the latest activated electrode. This will require such electrogram data to be transmitted to impedance cardiographic equipment 20 via electronic interface 20E which transmits such data between CRT device external programmer and processor 20D.

Figure 5:
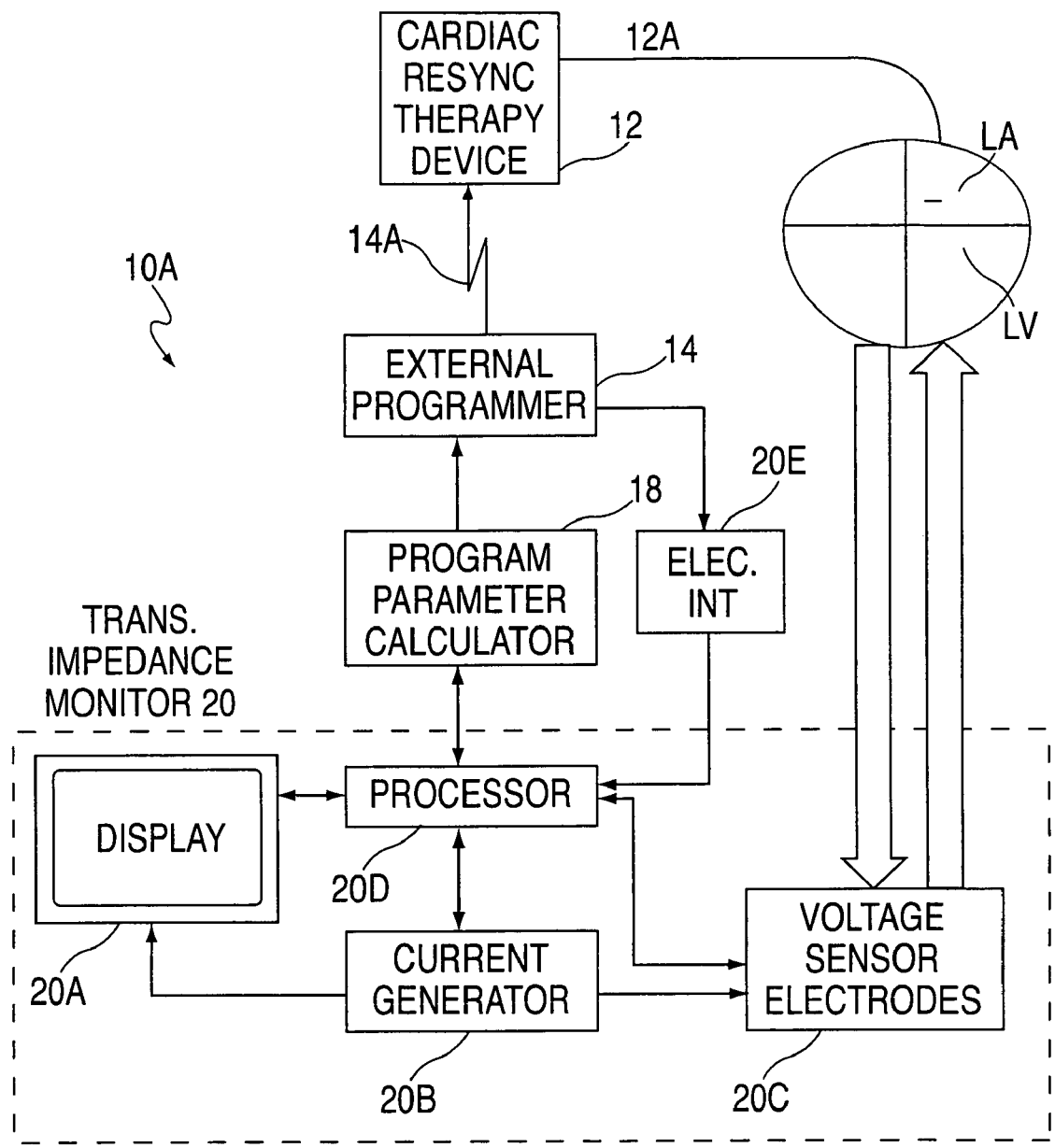
FIG. 5 shows a block diagram for an alternate embodiment with an external transthoracic impedance sensor.

The parameters described so far are determined using external means, i.e., ultrasonic equipment as described and shown in FIG. 1 or impedance cardiography equipment as described and shown in FIG. 5. In an alternate embodiment of the invention, parameters are determined using internal means. This latter approach has several advantages. One is that additional equipment is not required. A second advantage is that the programming of the CRT can be updated dynamically as a true closed loop system and will not require outside intervention. This is useful as a patient's condition is not static and changes in interval timing may need to be modified in different clinical situations such as when a patient has a heart attack or has progressive congestive heart failure. Parameters that can be derived in this manner are based on intra-thoracic or intra-cardiac impedance measurements.

It is conventional to measure intra-thoracic impedance using two spaced electrodes. A current is applied between one electrode and a reference electrode and the corresponding induced voltage is then measured at a second set of electrodes. If bipolar electrodes are used, the reference electrode can be the tip or the ring of bipolar electrode. The measurement can be repeated throughout the cardiac cycle thereby generating a time dependent impedance curve $Z(t)$.

Figure 7:
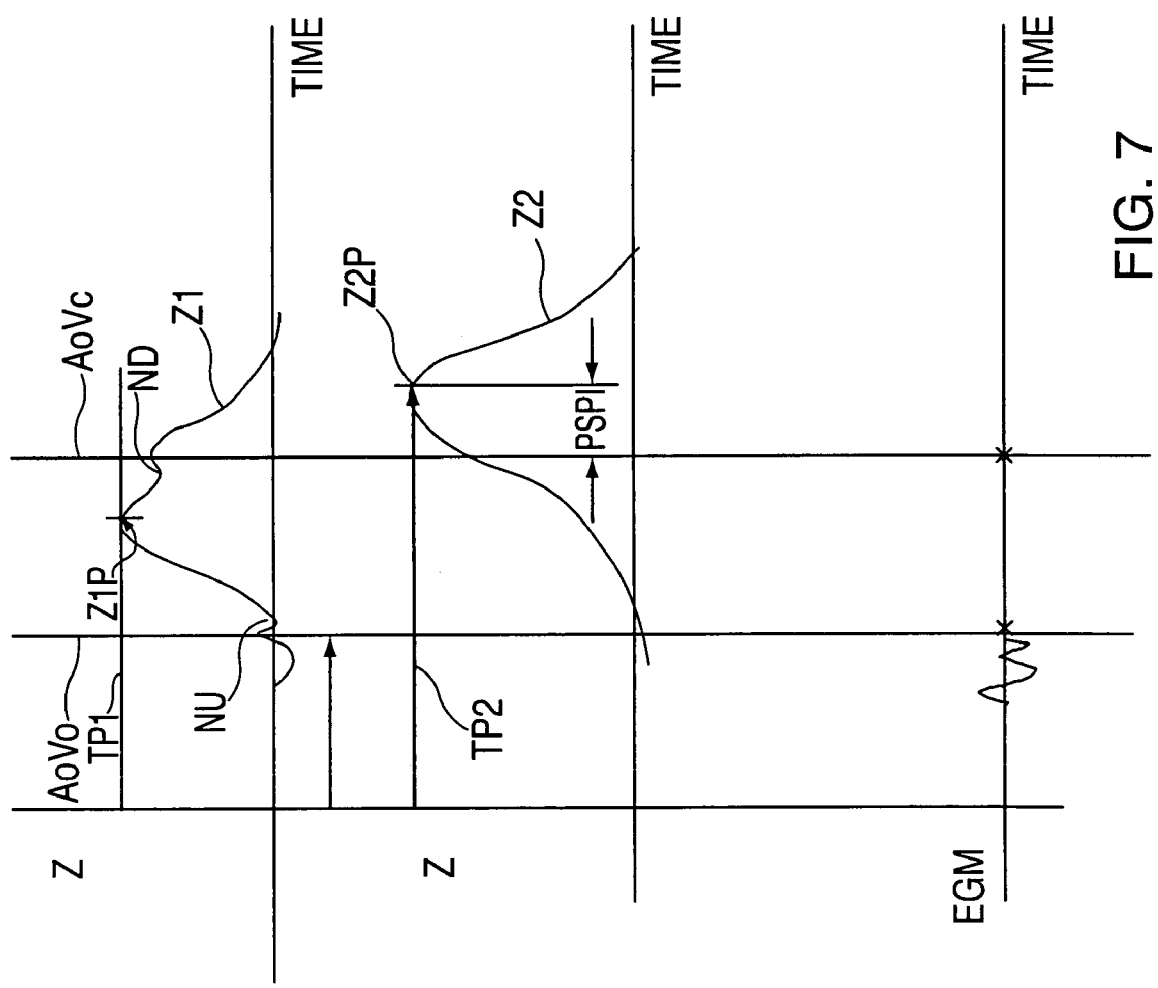
FIG. 7 shows time-dependent curves of impedance derived from transmyocardial electrodes in a dysynchronous portion of the left ventricle, $Z2p$, (middle) and derived from electrodes positioned in a trans-valvular location, $Z1p$, (top) as to delineate timing of aortic valve closure, wherein there is delayed systolic thickening and a corresponding increase in impedance after aortic valve closure (post-systolic positive impedance, PSPI) for impedance signal $Z2$, the intracardiac electrogram being denoted as a reference for all acquired signals as well (bottom)

As shown in FIG. 7, $Z1(t)$ starts with ventricular depolarization, and normally has a peak value $Z1p$ disposed between the AoVo, the time when the aortic valve opens and AoVc, the time that the aortic valve closes, referenced to a specific intracardiac electrogram signal, EGM. Certain optimally positioned electrodes will generate impedance signals such as $Z1p$ where timing of aortic valvular events by notches on the upslope, NU, and downslope, ND, of the impedance signal can be identified.

Similar Z curves can be generated between different electrodes attached to various myocardial segments. For example, turning back to FIG. 4, two electrodes 40 and 42 may be provided with electrode 40 being attached to the lateral wall of the left ventricle (coronary sinus lead), near region 36 and electrode 42 being attached to the right ventricular portion of the interventricular septum symmetrically with respect to electrode 40, near region 34. Ideally, the peak of the resulting impedance curves Z1, Z2 should occur at a synchronous point in time for symmetrically stimulated myocardial segments, at a time between aortic valve opening and aortic valve closure. However, in a heart with a pronounced AMD the two peaks may be shifted significantly. Therefore, in one mode of operation, the relative times to respective peak impedances $Z1p$, $Z2p$ (TP1, TP2 in FIG. 7) are determined, electromechanical time intervals, which are then used to define the electromechanical correction factor index, EMCFI defined by EMCFI=TP1/TP2. This factor is optimized in accordance with the technique described above, for the other embodiments of the invention, and is optimized when it is closest to unity. The parallel to EMCFI is the SCFI using ultrasound technology.

In another embodiment of the invention, the impedance curves are Z1 and Z2 with Z1 being associated with a right ventricular lead and Z2 being associated with a coronary sinus left ventricular lead. In this embodiment, the two ventricles are synchronized.

Figure 12:
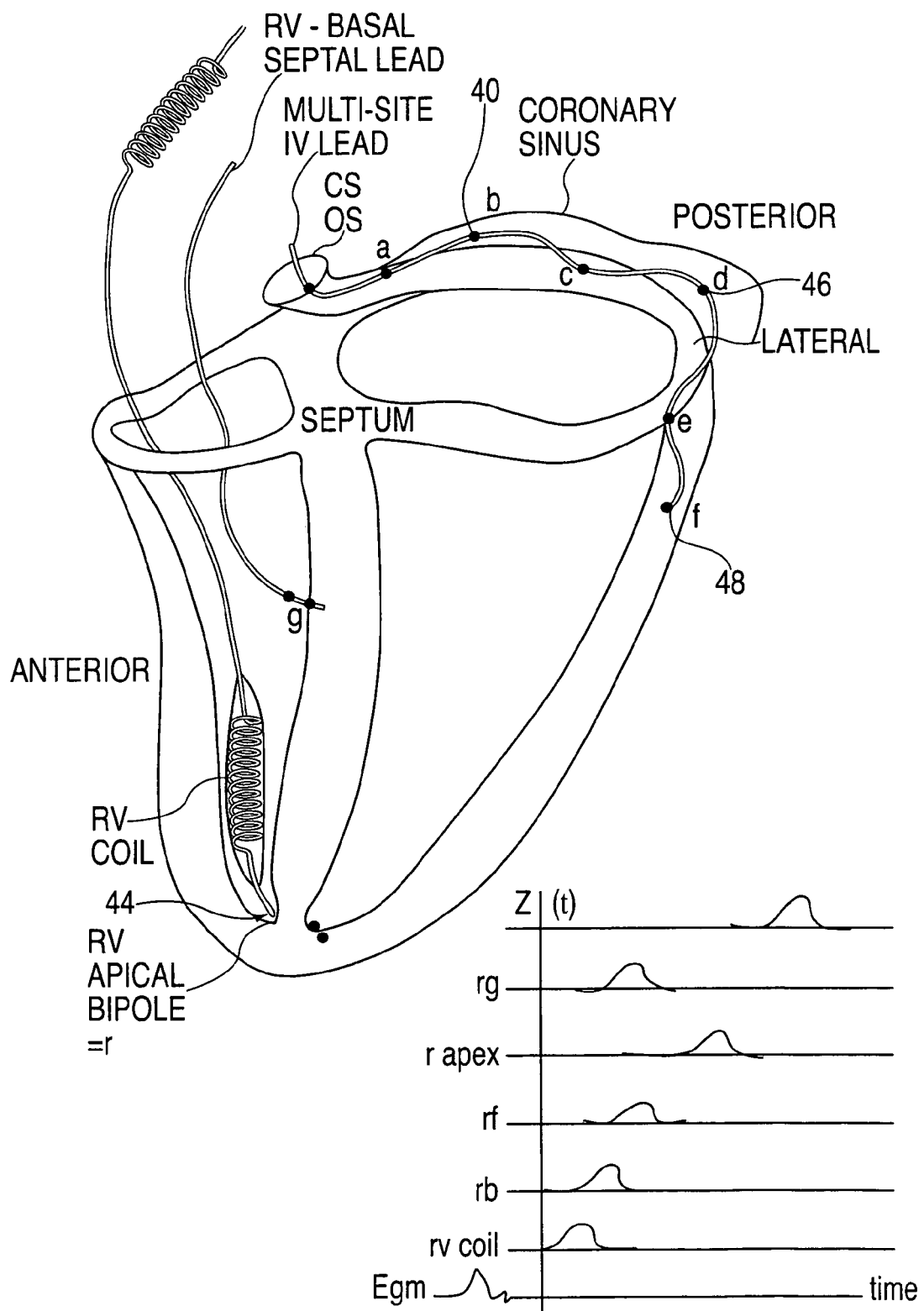
FIG. 12 shows bipolar electrodes radially located along a coronary sinus (CS) lead which describe the rotational or helical properties of the heart during the cardiac cycle.

In yet another embodiment, instead of just two impedance curves, several impedance curves are derived using different electrode pairs and the resulting time to peak impedance is measured between each set of electrodes as to determine the optimal sequence for stimulation between such multiple electrodes. For example, in FIG. 12, the electrode pairs may be defined between electrode 44 attached near the apex in the right ventricle and electrodes 40, 46, 48 placed radially along the coronary sinus, CS. Electromechanical timing sequences between such multiple electrode pairs can be compared to templates derived in the electrophysiology lab or from devices implanted in patients with favorable remodeling and reversibility of dysynchrony. Such a multi-site CS lead can measure pure intracardiac electrogram signals along the CS lead electrodes devoid of impedance data or data related to electromechanical delay times by using both electrogram and impedance signals. Data acquired in this fashion can direct programming of interval timing between such electrodes or be used for pure sensing purposes as to more accurately describe dysynchrony along the radial course of the coronary sinus lead. Such data will provide a window into the helical nature of systolic and diastolic coiling and uncoiling of the heart in multiple dimensions.

Figure 10B:
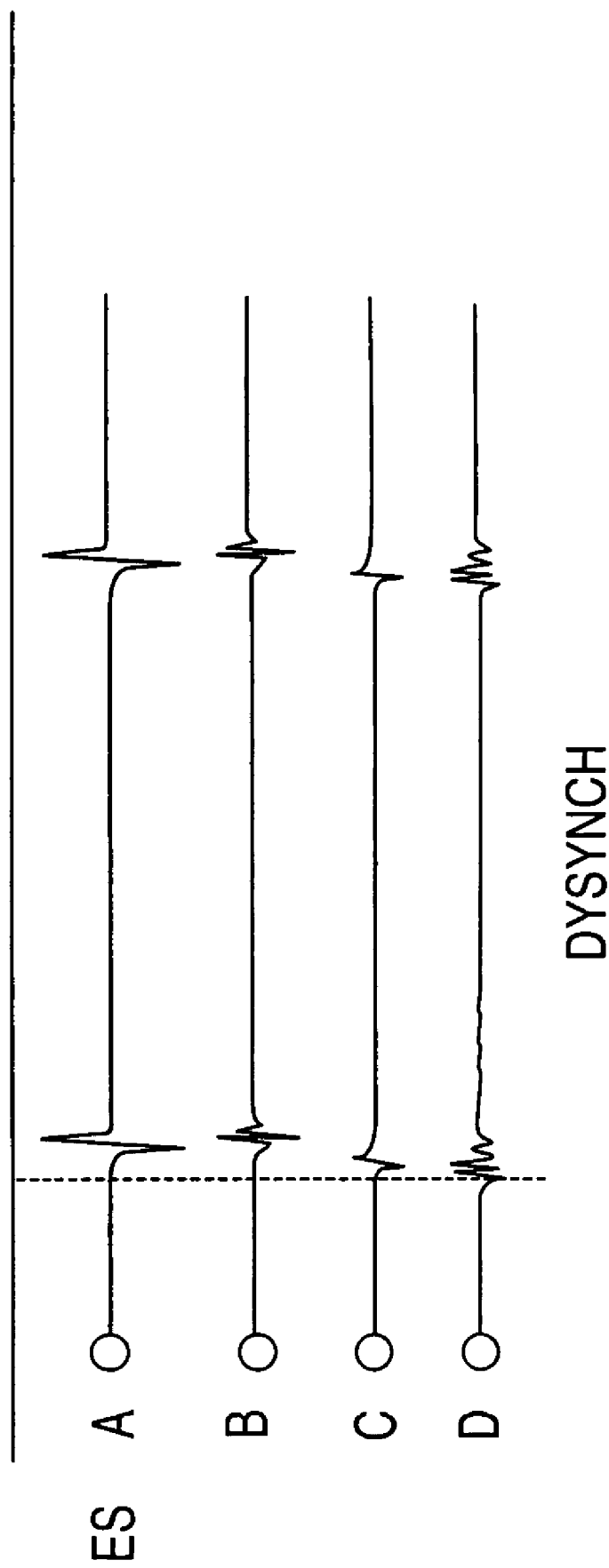
FIG. 10B shows intracardiac electrograms obtained from a multi-site coronary sinus lead in a patient with dysynchrony.

Similarly located electrodes can be used to identify electrical activation patterns without use of impedance data and serve to monitor AMD. Such an embodiment will require analysis of intracardiac electrogram signals along a multi-site coronary sinus lead. In a patient with more dysynchrony there will be more variability in timing sequences along such a lead (FIG. 10B) while once synchronized such activation patterns will occur more simultaneously (FIG. 10C).

Other parameters may be derived from the impedance curves and used in a similar manner, such as the integral of $Z(t)$, integral between specific time frames within a single impedance curve, first and second derivatives of $Z(t)$, derived and analyzed from single or multiple electrode pairs and so on. These latter parameters are internal cardiac performance parameters rather than anisotropic myocardial performance parameters and parallel, for example, external ultrasonic measurements of the aortic velocity time integral, or external thoracic impedance measurements of cardiac output. Such internally derived impedance data is associated with a baseline constant impedance value not related to dynamic changes in impedance during the cardiac cycle. As such this offset, which does not represent physiologically relevant data, is subtracted from the data acquired. Importantly, variations in impedance related to changes in lung volume from the respiratory cycle need to be removed from the impedance signal as well. This can be done in part by using higher frequency current pulses as to derive impedance data which in essence creates a band pass filter or by deriving impedance data at a specific time during the respiratory cycle (e.g. end-expiration). Similar signal processing is performed for impedance-derived determinations of AMD.

Figure 8:
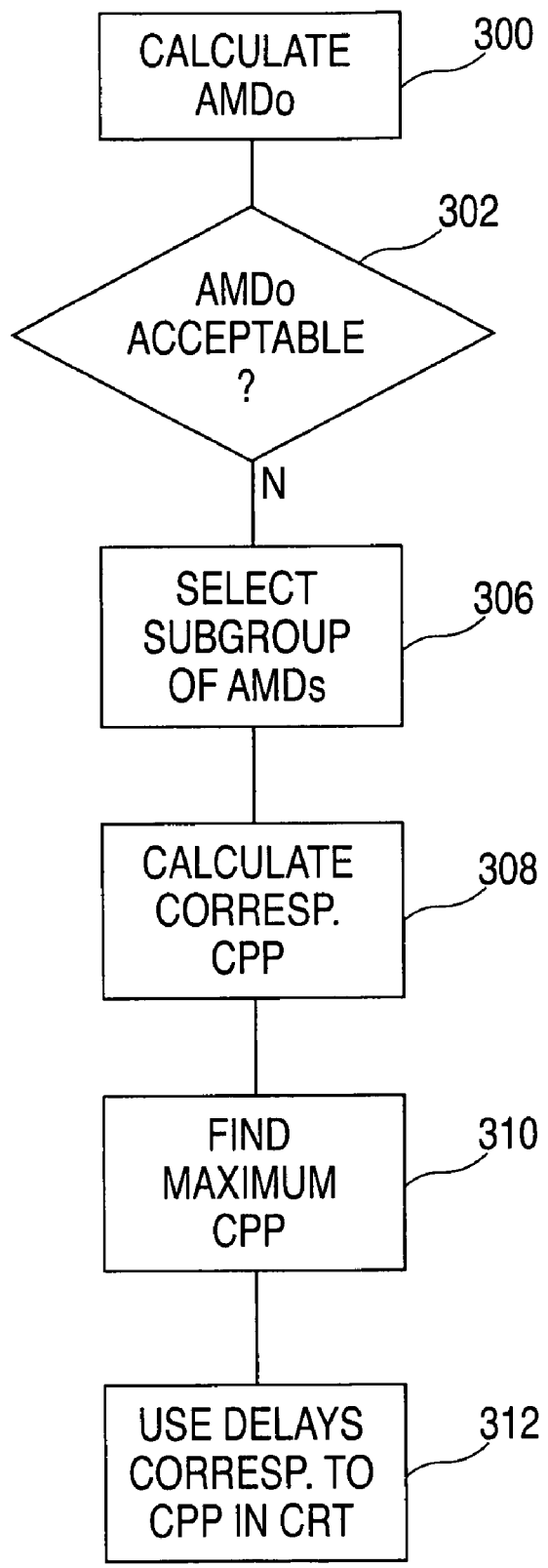
FIG. 8 shows a block diagram for an alternate embodiment of the invention.

In the embodiments discussed so far, an AMD parameter is determined that quantifies or otherwise indicates the degree of dysynchrony or a cardiac performance parameter, CPP, is determined which relates to cardiac output. Alternatively, both CPP and AMD parameters can be used as to describe the output of the heart, such as $dZ/dt$, and the degree of dysynchrony such as the EMCFI. In this embodiment of the invention as shown in FIG. 8 the therapeutic system utilizes blended measurements of cardiac performance and anisotropic myocardial deformation. This embodiment is useful as the selected AMD parameter may not necessarily represent synchrony at the appropriate time during the cardiac cycle. For example, though the EMCFI may approach unity, when the time to peak velocity for symmetrically located segments occurs near-simultaneously, both regions of interest may reach peak contractility at a less than optimal time with relation to the opening and closing of the heart valves. This is important to consider as acquisition of impedance curves that define valvular events may not be consistently obtained. This methodology is more vital to a true closed loop system using impedance derived parameters as valvular events can not be as readily defined as through connectivity with an ultrasonic interface. Starting with step 300, the optimal AMDo is calculated using any of the embodiments discussed above. In step 302 a determination is made whether the AMDo is acceptable. This determination is made, for example, by checking how close is the AMDo to a test or threshold value. For example, if AMDo is selected based on a target, in step 302 a check is performed to determine if AMDo is within a predetermined range. If the AMD is EMCFI, the target for these parameters is 1.0 and therefore a check in step 302 is made to determine whether 0.8<AMDo<1.2. Similarly, if in this example the quantitative AMD parameters determined through evaluation of set MxN interval timings follows a Gaussian distribution with a mean approaching one, a subset of intervals (AVa-VrVIa, AVb-VrVIb, AVc-VrVIc) which represent AMDo's that fall within one or two standard deviations of the mean EMCFI (in this example, EMCFIa, EMCFIb, EMCFIc) can become variables evaluated in step 308 using an internal CPP such as dZ/dt, peak Z, or $\int Z(t)dt$. If the AMDo is within this range, then it is accepted and a CPP parameter is evaluated for each AMDo within the specified range.

Once, in step 308 a CPP parameter is determined for each of the delay pairs in accordance, for example, the process is set forth as in FIG. 2. In step 310, the optimized CPPo is selected. In step 312 the corresponding delays are determined and the CRT is programmed using these delays as operational parameters.

Figure 11:
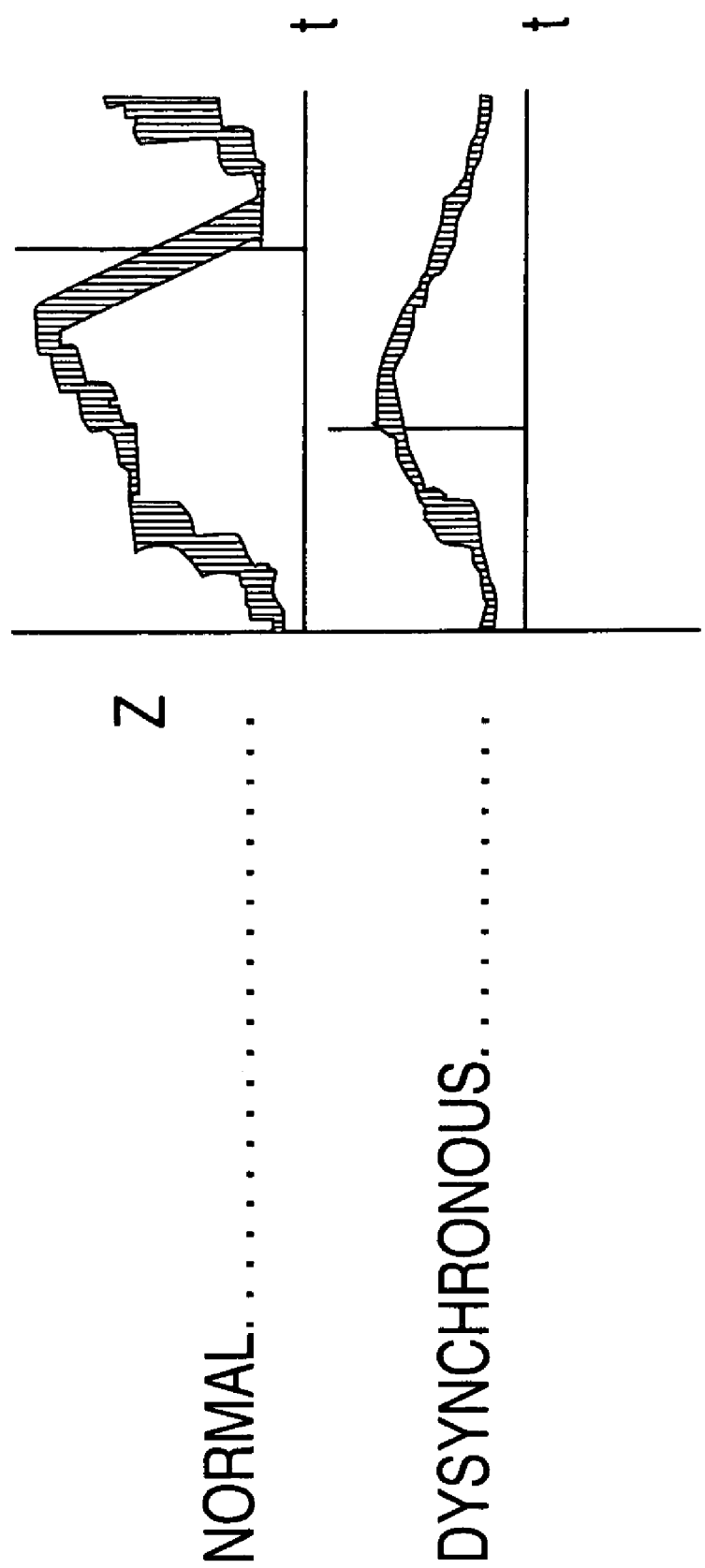
FIG. 11 shows the normal appearance of Z(t), top, which is usable as a normal template with a pathologic Z(t) signal, bottom, in a patient with advanced dysynchrony.

In yet another embodiment of this invention, comparisons of the morphology of optimal impedance waveforms (FIG. 11) and timing relationships relative to intracardiac electrograms along specific electrode vectors in a given patient (FIG. 10A) to those obtained in patients with normal electromechanical properties can be made. When the morphology of the impedance waveform and timing intervals in a given patient is most congruent with that of a normal template, an optimal CPP has been achieved (impedance waveform morphology congruence). As the integral under Z(t) and the shape of the impedance waveform is assessed as well as electromechanical delay times this parameter represents a blended analysis of AMD, CPP and electromechanical timing.

Figure 9:
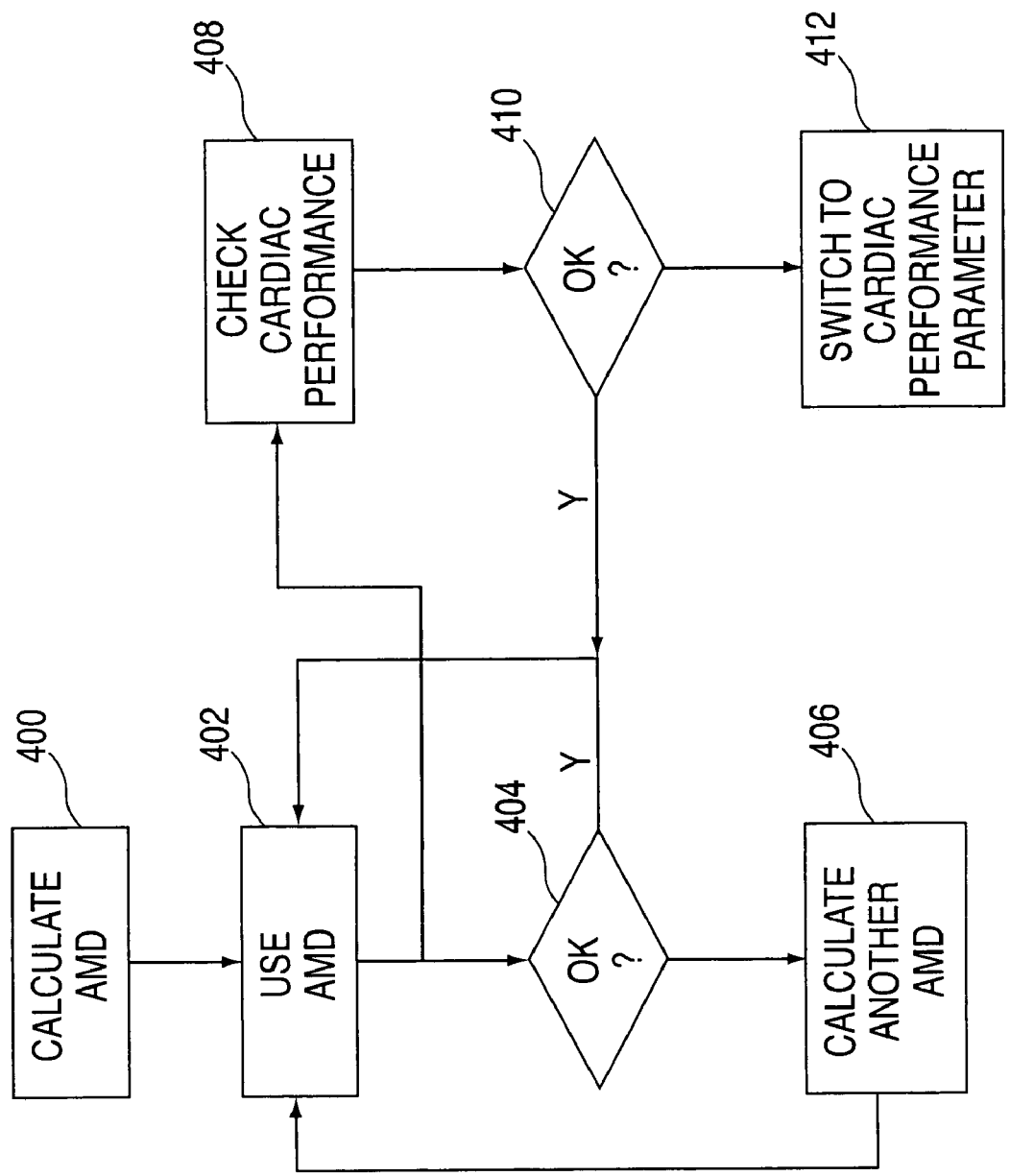
FIG. 9 shows a block diagram of an embodiment with parameter switching.

Importantly, as discussed above, since these parameters are measured internally, all calculations involving these parameters may be performed within the CRT itself. Therefore, the parameter calculator itself may be disposed in the CRT. Another advantage of this arrangement is that the programming parameters may be changed dynamically and automatically within the CRT without the programmer being available and the system behaves as a true closed loop system. This feature is important because various characteristics of the heart of a patient change over time, sometimes slowly, due to aging or a change (for better or worse) in the cardiac condition of the patient. Occasionally such characteristics may change rapidly, for example, in the presence of progressive congestive heart failure or as a result of exercise induced electromechanical dysynchrony. A mode of operation for the CRT is shown in FIG. 9. In step 400 the CRT 12 calculates an AMD parameter (e.g. EMCFI), as discussed above. In step 402 the parameter is used to determine the operational parameters of the CRT. At certain predetermined intervals, for example, once a day, or even dynamically after several cardiac cycles, or after any other programmable or periodic interval, the operation of the CRT, and or the condition of the patient is checked as part of a vital monitoring system. If the CRT or the heart H are functioning satisfactorily, then normal operation continues with step 402. If in step 404 it is found that the CRT is not operating in an optimal fashion, for example, if measurements of intra-thoracic and/or intracardiac impedance are consistent with values indicative of congestive heart failure (decreases in relative intra-thoracic impedance secondary to pulmonary vascular congestion and/or the presence of a marked discrepancy between impedance waveform morphology and the normal template) then in step 406 a new AMD parameter is implemented and used in step 402. If this second AMD is not acceptable, then the CRT can implement a different AMD parameter. In this fashion, the optimal AMD parameter for monitoring and directing programming of interval timing within the CRT device is identified and applied in the methodologies described above. This describes an automatic optimization algorithm, which serves as a control system for the CRT.

In another embodiment of the invention, the CRT is provided with an emergency default mode. The purpose of this feature is to detect and to take action if the heart H has undergone a sub-critical change (for example, dramatic reduction in transthoracic impedance secondary to acute pulmonary edema, and/or significant increases in minute ventilation) and therefore requires a different type of optimization algorithm or alternate pacing modality. Under this circumstance, instead of seeking to minimize AMD the system will switch as to maximize a CPP. This is depicted in FIG. 9. For this purpose, at regular intervals, for example, the cardiac output of the heart is evaluated (e.g. $\int Z(t)dt$), in step 408 as a measure of cardiac performance. If in step 408 it is determined that the heart has not improved, then in step 412 the CRT chooses a different CPP. In this example, in a sub-critical clinical circumstance a parameter is chosen that has been selected to optimize cardiac output rather than a parameter meant to minimize AMD. In the short term it may be beneficial to direct the system to purely increase cardiac performance rather than minimize AMD and rather than optimizing any blended parameters that reflect both CPP and AMD. Though these endpoints may be reached with similarly programmed parameters (interval timing), situations in the acute setting may be best treated by maximizing cardiac performance. Minimization of AMD will be more beneficial in the long term and promote favorable remodeling whereas maximization of cardiac performance may increase myocardial demands at the expense of long term benefit. This has been demonstrated with pharmaceutical agents that increase cardiac performance (inotropic drugs). When used chronically, these agents are associated with an increased risk of arrhythmia and increased mortality. Nonetheless, such agents improve congestive heart failure in the acute setting.

The CRT then operates in this mode of optimizing a CPP either for a preselected time, until another check indicates that the latter mode is no longer required, or until the patient sees his physician. In the event of a more critical change in status this control system may employ novel methods of stimulating the heart that augment cardiac performance with use of high energy current delivery that serve to better recruit relatively denervated myocardium. The latter embodiments are described in conjunction with the same flow chart, however, it should be understood that they can be implemented independently of each other.

Such a control system is also important as changes in the system (e.g. reduced functionality of specific electrodes) may impair its ability to monitor certain parameters (e.g. $\int Z(t)dt$) or inadequate signal to noise ratios may cause an inability to delineate timing of valvular events. In such a circumstance, changes in the patients clinical status may occur and require use of an alternate parameter that is less dependent upon the previously employed, less reliable, algorithm or necessitate use of a more simplified means of defining the optimal programmed parameters as described below in the next embodiment.

In this simplified embodiment, changes in interval timing can be made without use of the above described matrix optimization methods for determining interval timing. In this embodiment, intra-thoracic impedance measurements can be made at periodic intervals and re-evaluated as delay times are varied without assessment of an AMD or CPP parameter. This automatic optimization algorithm relies on more chronic monitoring data than use of an AMD parameter or CPP as trends in pulmonary vascular congestion as a result of variations in interval timing will occur over more extended periods of time. Such an algorithm will be less dependent on multiple electrodes and impedance signals and be less prone to impaired functionality. Such an algorithm will also have less demands on microprocessor robustness and may be pragmatic in many situations but will not have the sensitivity and specificity of the more complex embodiments described. As such, such a system will not be as capable of making dynamic changes in programmed parameters but will still serve to improve the functionality of current CRT systems without the need for more complex algorithms.

In summary, in the present invention, means are provided for quantifying and comparing cardiac performance and/or anisotropic myocardial deformation using electrical and/or mechanical properties analyzed either extrinsically or intrinsically. This information is used for providing a resynchronization device with a control system capable of optimizing cardiac performance and/or minimizing anisotropic myocardial deformation both in the acute and chronic setting. Moreover the resulting operation is optimized for a given patient, based on measurements specific for the individual patient.

I claim:

1. An apparatus for programming an implantable medical device comprising:
    a programmer that provides operational parameters to the implantable medical device;
    an impedance measuring device that measures an intra-thoracic impedance between two spaced apart electrodes and determines a programming parameter for a patient's heart based on said intra-thoracic impedance; and
    a calculator receiving said programming parameter and generating said operational parameter for said programmer.

2. The apparatus of claim 1 wherein said programmer applies a plurality of stimulations to the patient's heart and said calculator monitors the resulting programming parameter and selects the optimal programming parameter and the corresponding operational parameter.

3. The apparatus of claim 1 wherein said monitor is implemented in the implantable medical device.

4. The apparatus of claim 1 wherein said programming parameter is indicative of cardiac performance.

5. The apparatus of claim 1 wherein said programming parameter is determined from a plurality of functions, each function being associated with a myocardial region during a cardiac cycle.

6. An apparatus for programming an implantable medical device, comprising:
    a programmer that provides operational parameters to the implantable medical device;
    a monitor that measures myocardial strain of specific regions of a patient's heart and determines a programming parameter for the patient's heart based on the measured strain; and
    a calculator receiving said programming parameter and generating said operational parameter for said programmer.

7. An apparatus for programming an implantable medical device, comprising:
    a programmer that provides operational parameters to the implantable medical device;
    a monitor that measures myocardial velocity from specific regions of a patient's heart and determines a programming parameter for the patient's heart based on said myocardial velocities; and
    a calculator receiving said programming parameter and generating said operational parameter for said programmer.

8. The apparatus of claim 7 wherein said monitor is external.

9. The apparatus of claim 7 wherein said monitor is ultrasonic equipment.

10. The apparatus of claim 9 wherein said programming parameter is indicative of anisotropic myocardial deformation, (AMD).

11. An apparatus for programming implantable medical device comprising:
    equipment that monitors several programming parameters;
    a calculator that selects an optimal parameter from said programming parameter and generates an operational parameter for said implantable medical device based on said optimal parameter, wherein said programming parameters depend on one of strain or velocity.

12. The apparatus of claim 11 wherein said calculator generates said optimal parameter based on one of cardiac performance and/or anisotropic myocardial deformation, (AMD).

13. An apparatus for programming implantable medical device comprising:
    equipment that monitors several programming parameters;
    a calculator that selects an optimal parameter from said programming parameter and generates an operational parameter for said implantable medical device based on said optimal parameter, wherein said programming parameters are based on Doppler ultrasound quantification of velocity of multiple pre-selected myocardial regions during a cardiac cycle.

14. The apparatus of claim 13 wherein said equipment comprises ultrasonic equipment for measuring myocardial strain in specific areas of interest.

15. An implantable medical device comprising:
    equipment that monitors a programming parameter; and
    a calculator that selects an optimal value for said programming parameter and uses said optimal value to generate an operational parameter, said operational parameter defining the normal mode of operation of said implantable medical device, wherein said equipment monitors an anisotropic myocardial deformation parameter and a cardiac performance parameter and said calculator selects the optimal value on both said anisotropic myocardial deformation and cardiac performance parameters.

16. The implantable medical device of claim 15 wherein said calculator monitors the performance of the heart and under certain pre-determined sub-critical or critical conditions switches from an operational parameter based on anisotropic myocardial deformation to an operational parameter based on cardiac performance.

* * * * *

UNITED STATES PATENT AND TRADEMARK OFFICE
CERTIFICATE OF CORRECTION

| | | |
|---|---|---|
| PATENT NO. | : 7,065,400 B2 | Page 1 of 1 |
| APPLICATION NO. | : 10/779162 | |
| DATED | : June 20, 2006 | |
| INVENTOR(S) | : Stuart O. Schecter | |

It is certified that error appears in the above-identified patent and that said Letters Patent is hereby corrected as shown below:

Title Page, Item (12) inventor's name should read -- Schecter --.

Item (75) inventor's name should read -- Stuart O. Schecter --.

Signed and Sealed this

Twenty-seventh Day of April, 2010

David J. Kappos
*Director of the United States Patent and Trademark Office*